(12) United States Patent
Seitz et al.

(10) Patent No.: US 6,488,202 B1
(45) Date of Patent: Dec. 3, 2002

(54) DEVICE AND METHOD FOR IDENTIFYING A SIZE OF AN ABSORBENT ARTICLE WHICH IS FIT-APPROPRIATE FOR A POTENTIAL WEARER

(75) Inventors: Bret D. Seitz, West Chester, OH (US); Gary D. Lavon, Cincinnati, OH (US); David M. Weirich, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/539,763

(22) Filed: Mar. 31, 2000

(51) Int. Cl.[7] .............................................. G06C 27/00
(52) U.S. Cl. ................................................... 235/78 R
(58) Field of Search .......................... 235/78 R, 78 RC

(56) References Cited

U.S. PATENT DOCUMENTS

| | | | | |
|---|---|---|---|---|
| 2,406,495 A | * | 8/1946 | Grand-Jean | 35/56 |
| 4,149,068 A | * | 4/1979 | Simon | 235/78 R |
| 4,454,409 A | * | 6/1984 | Sehres | 235/78 R |
| 5,880,974 A | * | 3/1999 | Tarumi et al. | 364/578 |
| 5,992,072 A | | 11/1999 | Mack | 33/12 |

OTHER PUBLICATIONS

Package from No Nonsense® Great Shapes® Pantyhose.

* cited by examiner

Primary Examiner—Michael G. Lee
Assistant Examiner—Lisa M. Caputo
(74) Attorney, Agent, or Firm—Michael P. Hayden; David M. Weirich; Ken K. Patel

(57) ABSTRACT

A device and method are described for identifying the size of a disposable diaper or absorbent article which is appropriate in terms of proper fit for a potential wearer of the article. The device and method employ information regarding at least two different selected characteristics of potential wearers and an association between such information and a size of the article which is fit-appropriate for a potential wearer. The size identification is more reliable than an identification which is based solely upon a single characteristic of the potential wearer.

60 Claims, 10 Drawing Sheets

DEVICE AND METHOD FOR IDENTIFYING A SIZE OF AN ABSORBENT ARTICLE WHICH IS FIT-APPROPRIATE FOR A POTENTIAL WEARER

FIELD OF THE INVENTION

The present invention is directed to a device and method for identifying a size of a disposable diaper or other article which is appropriate in terms of proper fit for a potential wearer of the article.

BACKGROUND OF THE INVENTION

Disposable diapers and other absorbent articles are designed to absorb and contain liquid and other discharges from the human body to prevent body and clothing soiling. Disposable diapers, as one example, have a variety of designs, each typically available in a range of sizes. The size of the diaper typically affects, for example, the size of the diaper waist opening, the size of the openings around the thighs, and the length or "pitch" of the diaper. If a person such as a consumer selects a diaper which is size-inappropriate for a potential wearer, the waist opening, thigh openings or pitch of the diaper, for instance, may be too large for proper fit on the wearer, potentially leading to slipping, sliding, sagging, drooping, or a loss of gasketing effects that are designed to inhibit leakage. Alternatively, the waist opening, thigh opening or pitch of a size-inappropriate diaper may be too small for proper fit, potentially leading to wearer discomfort or skinmarking of the wearer's skin.

Currently, disposable diapers are typically sold in packages which are labeled with a "size number" and a recommended wearer weight range. For example, a package labeled "Size 3" may include information that the recommended wearer weight range for the diapers included in the package is from about 16 to 28 pounds (about 7 to 13 kg). As a result, weight is often the sole criteria used to identify a diaper size and thereby select a particular-sized diaper for a potential wearer. This is the case even though other characteristics and anthropometric attributes of potential wearers (for example, age, height, waist circumference, thigh circumference, and rise) may vary widely within the recommended weight range, and may result in an ill-fitting diaper even though a wearer's weight falls within that range.

Further complicating the typical situation with respect to the identification and selection of size-appropriate disposable diapers is the presence of a significant overlap, from one "size number" to the next, of the recommended weight ranges on the associated packages. For example, a "Size 2" diaper may have a recommended weight range from about 12 to 18 pounds (about 5 to 8 kg), a "Size 3" diaper may have a recommended weight range from about 16 to 28 pounds (about 7 to 13 kg), and a "Size 4" diaper may have a recommended weight range from about 22 to 37 pounds (about 10 to 17 kg). A "Size 5" or greater diaper may have a recommended weight range with no upper limit. Such overlaps or lack of upper weight limits may lead to consumer confusion or a lack of faith that the recommended weight ranges alone are reliable means of identifying the size of a diaper which is fit-appropriate for the potential wearer.

Thus, there is a need for a device and method which can more reliably identify the size of a disposable diaper or other absorbent article which is fit-appropriate for a potential wearer.

SUMMARY OF THE INVENTION

The present invention is directed to a device and method for identifying a size of a disposable diaper or other absorbent article which is fit-appropriate for a potential wearer of the article.

The device of the invention employs information regarding a size or sizes of a disposable diaper or other absorbent article and an association between the size information and information regarding at least two different selected characteristics of potential wearers to identify a disposable diaper or other article which is sized appropriately in terms of proper fit for potential wearers who possess particular values for such characteristics. By way of example, the device of the invention can be a chart, graphic, table or list which includes size information associated with information regarding two or more selected characteristics of potential wearers in a manner which identifies, or which allows a person such as a consumer to identify, a size of disposable diaper or other absorbent article which is appropriate for a potential wearer possessing particular values for each of the selected characteristics. As another example, the device can be a computer or other interactive device which includes size information associated with information regarding selected potential wearer characteristics, and which allows a person to input values for the selected characteristics and then provides information identifying the size of disposable diaper or other absorbent article which is fit-appropriate for a wearer possessing characteristics having such values. Apparatus which enables a person such as a consumer to readily ascertain such values relative to a particular wearer are also described.

The method of the invention, in one aspect, involves selecting at least two different characteristics possessed by potential wearers of a disposable diaper or other absorbent article, developing an association between values for each of the characteristics and a size of the absorbent article which is fit-appropriate for potential wearers who possess particular values for such characteristics, and providing a medium which conveys information identifying or which allows a person such as a consumer to identify the size of disposable diaper or other absorbent article which is fit-appropriate for a wearer who possesses particular values for each of the characteristics. The medium can convey such size information visually, audibly or otherwise.

In another aspect, the present invention provides a method for identifying a fit-appropriate size of a disposable diaper or other absorbent article for potential wearers based upon the values of at least two wearer characteristics which are preferably known or readily ascertained by a person such as a consumer and which also takes into account at least two, and more preferably at least three, underlying anthropometric attributes of the wearers as well as attributes of the diaper or other article itself which are important to fit. The method can also be employed in developing a device which can be used to reliably identify an appropriately sized disposable diaper or other absorbent article.

The devices and methods of the invention can be utilized to provide meaningful guidance to a person such as a consumer, enabling the person to identify and select size-appropriate disposable diapers or other absorbent articles more reliably than an identification or selection based solely upon a single wearer characteristic such as a wearer's weight. Certain aspects of the invention can also be utilized to develop simplified relationships between anthropometric attributes of potential wearers which are important to article fit and other selected wearer characteristics. The foregoing devices and methods can be employed relative to disposable diapers and other absorbent articles having a range of sizes and a variety of designs.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

The present invention relates to a device and method for identifying a size of disposable diaper or other absorbent article which is fit-appropriate for a potential wearer of the diapers or other article. (However, the method may also be used to identify the appropriate size for a reusable garment.) The device and method of the invention utilize an association between a fit-appropriate size of the article and values of at least two characteristics of potential wearers. To ensure that the size identification is reliable, the aforesaid association is preferably based on relationships developed between such wearer characteristics and at least two, more preferably at least three, underlying fit-significant wearer attributes.

As used herein, the term "absorbent article" refers to devices which are designed to absorb and contain body exudates, and, more specifically, refers to devices which are placed within, against, or in proximity to, the body of the wearer to absorb and contain the various exudates discharged from the body. As used herein the term "diaper" refers to an absorbent article generally used by infants and incontinent persons that is worn about the lower torso of the wearer. It should be understood, however, that the present invention is applicable to other absorbent articles such as incontinence briefs, incontinence undergarments, diaper holders and liners, feminine hygiene garments, bandages, bibs, wraps and the like and to wearable articles such as underwear, pants and swimwear. The term "disposable" is used herein to describe absorbent articles which are not intended to be laundered or otherwise restored or reused as an absorbent article (in other words, they are generally intended to be discarded after a single use, and, preferably, to be disposed of in an environmentally compatible manner). References to identifying a "size" is used herein to include a direct or indirect identification of a garment disposable diaper or other absorbent article size, such as by number or letter (for example, "Size 3" or "Size A"), by direct description (for example, "Small" or "Large"), by indirect description (for example "Newborn" or "Toddler"), by word association (for example, "Little Mouse" or "Big Mouse"), by color association (for example, use of one color to signify one size and a different color to signify a different size), by use of graphics (for example, using a picture of reclining infant to signify a smaller size diaper and using a standing baby to signify a larger size diaper), or by any combination thereof, and whether expressed or discernible visually, audibly or otherwise. An "association" between a fit-appropriate size of the article and values of at least two characteristics of potential wearers also contemplates the reverse, i.e., an association between at least two characteristics of potential wearers to a fit-appropriate size of the article, and vice-versa.

Figure 1:
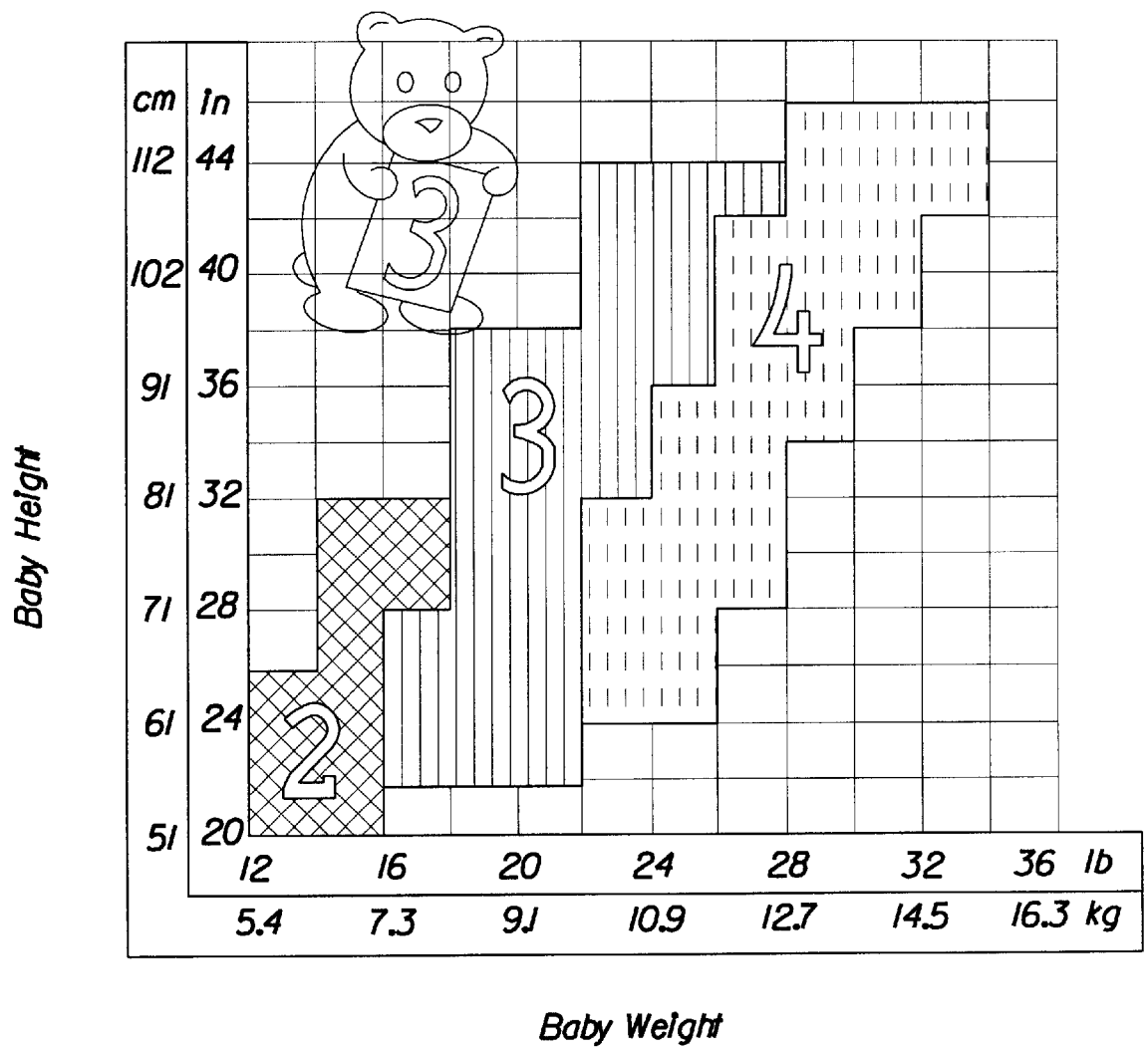
FIG. 1 is a plan view of a sizing guide.

One preferred embodiment of a device of the invention, in the form of a chart for identifying the size of a fit-appropriate disposable infant diaper, is shown in FIG. 1. The chart of FIG. 1 includes information corresponding to Sizes 2, 3 and 4 of a diaper having a design to which the chart relates. The chart also includes a vertical axis, a horizontal axis, a grid forming a matrix of rectangles adjacent the axes. The vertical axis is identified with the wearer characteristic "Baby Height", and includes potential wearer (baby) height values. The horizontal axis is identified with the wearer characteristic "Baby Weight", and includes potential wearer (baby) weight values. The information corresponding to each respective diaper size includes a diaper size number and a related series of rectangles in the matrix. (The rectangles may be replaced by any other suitable shape and may be colored or otherwise identified to fall within a certain size range.) Each rectangle corresponding to a particular size is associated with a potential wearer height value (actually representing a value range) included in the vertical axis and potential wearer weight value (also representing a value range) included in the horizontal axis, in other words, the rectangle is associated with a combination of a height value and a weight value. The association between a rectangle corresponding to a diaper size and the combined vertical and horizontal axis values for height and weight identifies the size diaper which is fit-appropriate for a potential wearer who possesses corresponding height and weight values. For example, the chart of FIG. 1 identifies a size 2 diaper as being fit-appropriate for an infant who possessed a weight value of 6 Kg and a height value of 55 cm.

The chart shown in FIG. 1 is particularly suited for use on a package of Size 3 diapers, given that information relating to "Size 3" and only the next smaller and larger sizes ("Size 2" and "Size 4") is provided. The bear and associated graphic illustrated on FIG. 1 provide an example of other types of information, not directly relevant to the present invention, which could also be included in a device along with information which is directly relevant to the invention.

Figure 2:
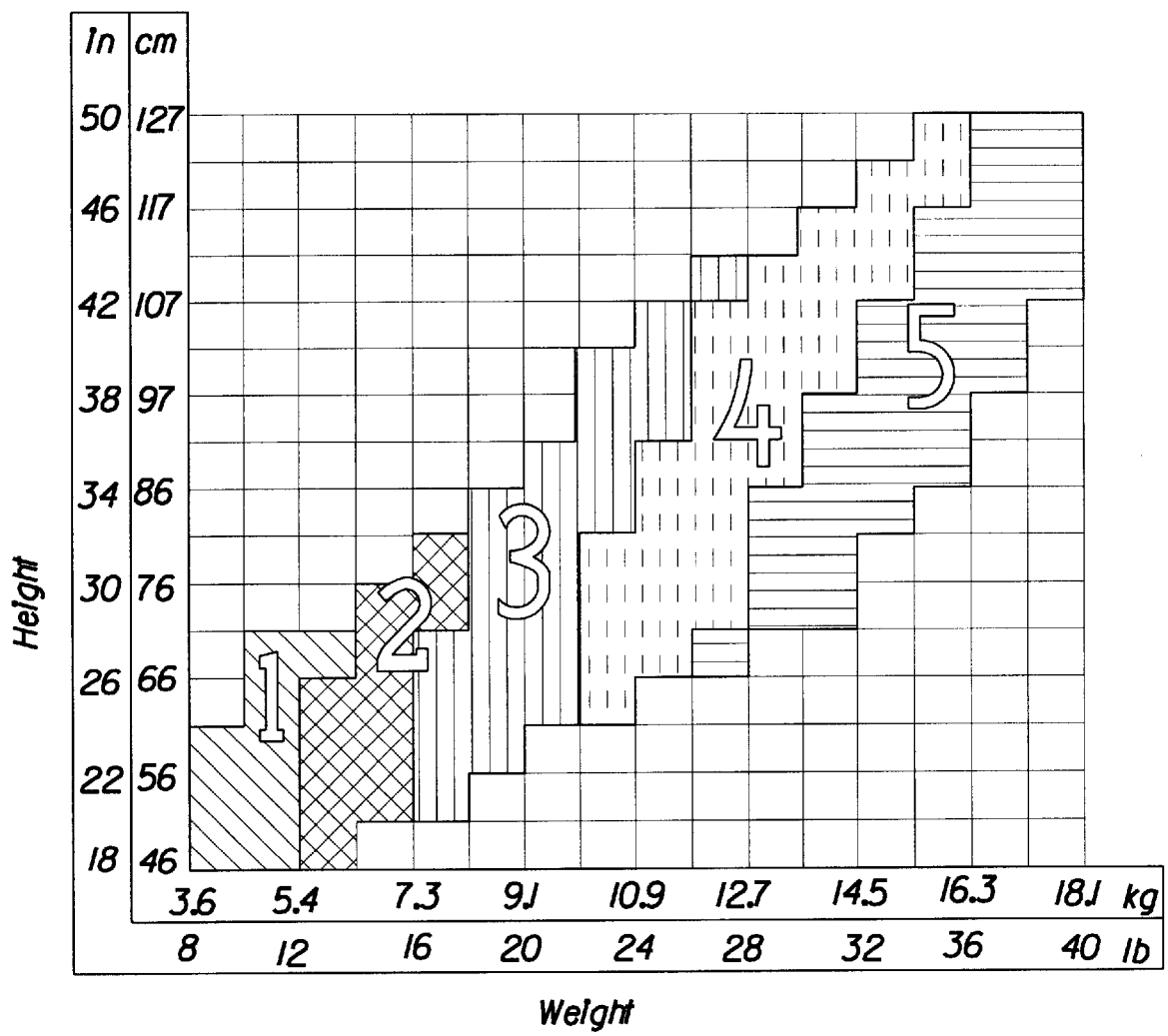
FIG. 2 is a plan view of another sizing guide.

Another preferred embodiment of a device of the invention, in the form of a chart for identifying the size of a fit-appropriate disposable infant diaper, is shown in FIG. 2. The chart of FIG. 2 includes information corresponding to Sizes 1, 2, 3, 4 and 5 of a diaper having a design to which the chart relates. The chart also includes a vertical axis, a horizontal axis, a grid adjacent the axes forming a matrix of rectangles. The vertical axis is identified with the wearer characteristic "Height", and includes potential wearer height values. The horizontal axis is identified with the wearer characteristic "Weight", and includes potential wearer weight values. The information corresponding to each respective diaper size includes a diaper size number, and a related series of colored (or otherwise identified) rectangles in the matrix. Each rectangle corresponding to a particular size is associated with the combination of a potential wearer height value (actually representing a value range) included in the vertical axis and potential wearer weight value (also representing a value range) included in the horizontal axis. The association between a rectangle corresponding to a diaper size and the combined vertical and horizontal axis values for height and weight identifies the size diaper which is fit-appropriate for a potential wearer who possesses a corresponding height and weight value combination. For example, the chart of FIG. 2 identifies a size 4 diaper as being fit-appropriate for a child who possessed a weight value of 11 Kg and a height value of 75 cm.

The chart shown in FIG. 2 is particularly well suited for use on or as at least part of an in-store display where Sizes 1–5 of the diaper to which the chart relates are offered for sale. The chart is also well suited for use in print or electronic advertising, promotional materials, or in other contexts in which information is presented regarding diapers which are available in a series of sizes. For example, the information presented in a chart such as that shown in FIG. 2 would be suitable for display on a diaper-related web page which could be accessed through the World Wide Web, also known as the Internet. The chart shown in FIG. 2 is also suitable for use on diaper packages.

The charts of FIGS. 1 and 2 also illustrate a medium which can be employed in connection with a method of the invention which conveys information identifying, or which allows a person, such as a consumer, to identify the size of disposable diaper or other absorbent article which is fit-appropriate for a wearer who possesses particular values for at least two selected wearer characteristics.

The invention also contemplates various other devices in which size information is associated with information regarding at least two different selected characteristics of a potential wearer to identify a size which is fit-appropriate for a wearer possessing particular values for those characteristics. For example, in addition to a chart, devices and methods of the invention may employ a graphic, table or list associating the size of a fit-appropriate disposable diaper or other absorbent article with wearer characteristic information. The chart, graphic, table or list could be employed, without limitation, on packaging for the article, in advertising or on promotional materials, or as part of an in-store display. The chart, table, graphic or list could be also displayed, without limitation, on printed media or electronically such as on an electronic display screen. Further, the device could also be used to provide the consumer or caregiver with information other than a size of an article. Such additional information could be in any form, and preferably relates to the baby specific information input into the device. For example, the device could provide the user with the baby's percentile rank relative to other babies based on information (e.g. weight and/or height) provided by the caregiver and a normal statistical analysis of the population of baby characteristics already collected and in a database.

Devices which require or permit active interaction (such as manual manipulation or other inputting of information to the device, including to a component thereof) on the part of a person such as a consumer are also contemplated. For example, a mechanical device such as a dial could be employed which permits a person to actively "dial in" information regarding the characteristics of the potential wearer of interest, and which would then identify or allow the person to identify a size of garment, disposable diaper or other absorbent article which is fit-appropriate for that wearer. An interactive device including one or more computers, handheld devices, scanners, etc. can also be utilized, which could prompt a person such as a consumer or caregiver to actively input answers to questions regarding the pertinent characteristics of the potential wearer of interest, keep track of the answers, and provide output information identifying or allowing the person to identify a size of garment, disposable diaper or other article appropriate for that wearer based on those answers. Such an "actively interactive" device could be employed as part of an interactive in-store display, as part of an interactive site on the World Wide Web, or as part of an interactive menu-driven phone system. Size identification information could be provided or output visually in the form of a chart, table, figure, symbol or other size indicia, or could be provided or output audibly such as through a message from an interactive phone system. As would be understood by those skilled in the art, where devices or methods of the invention employ a computer or computers, an electronic database could be used to associate size information regarding fit-appropriate garments, disposable diapers or other absorbent articles to values or ranges of values for at least two characteristics of potential wearers. These interactive devices, could be further enhanced by permitting the user to determine or influence the specific weighting factors and/or attribute targets (described in more detail below) so as to customize the size information provided to that person to their specific individual tastes. For example, the device or method of the present invention could include questions or other prompts which determine or help the user determine information relevant to the weighting factors and attribute targets. In one embodiment, the weighting factors or attribute targets could be adjusted by the user selecting preferred visual or graphical representations of the article to be fitted to the wearer from a group of pictures or graphics showing the article fitting differently on the same or different wearers.

Figure 4A:
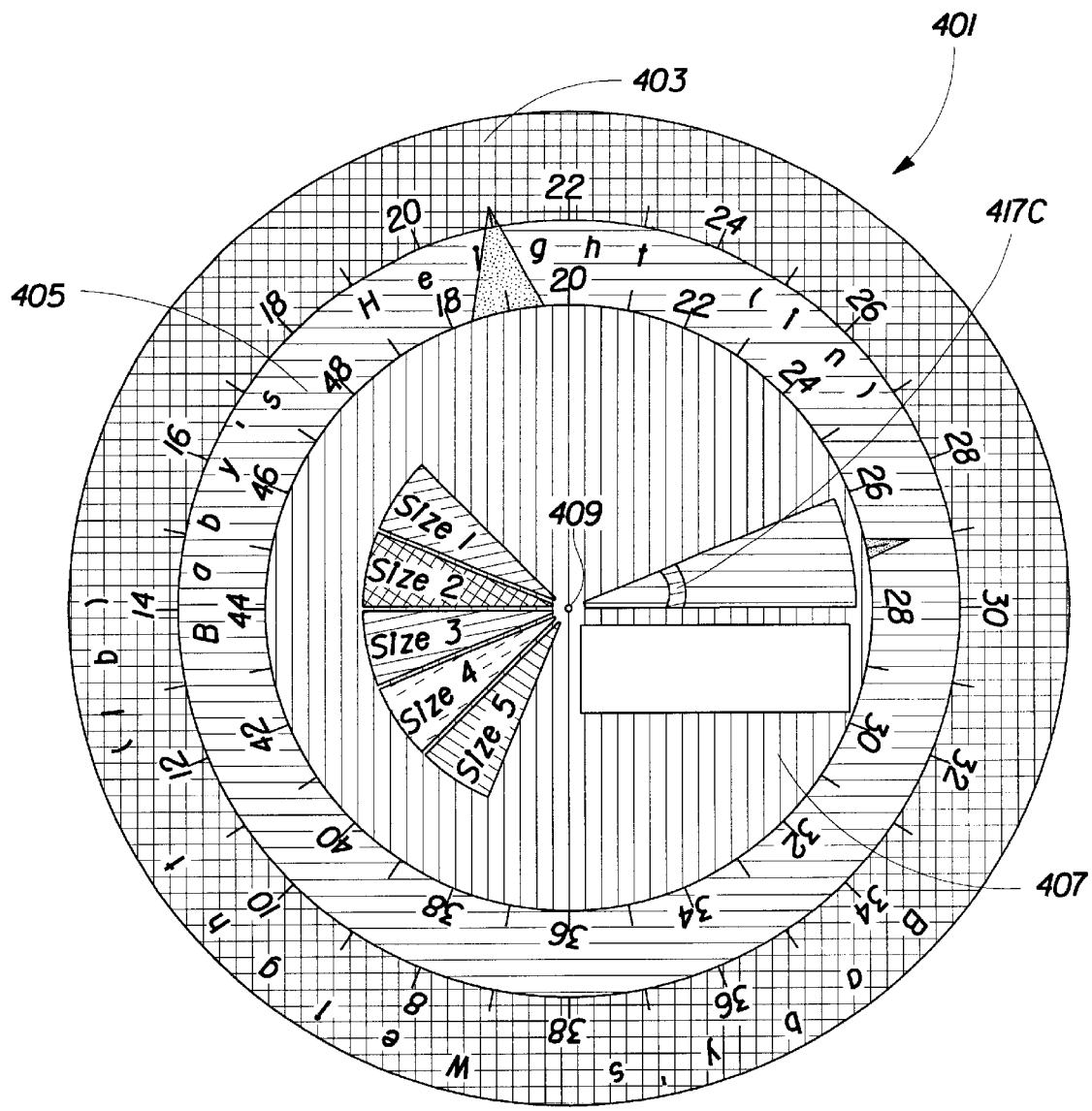
FIG. 4A is a plan view of a sizing guide wheel
Figure 4B:
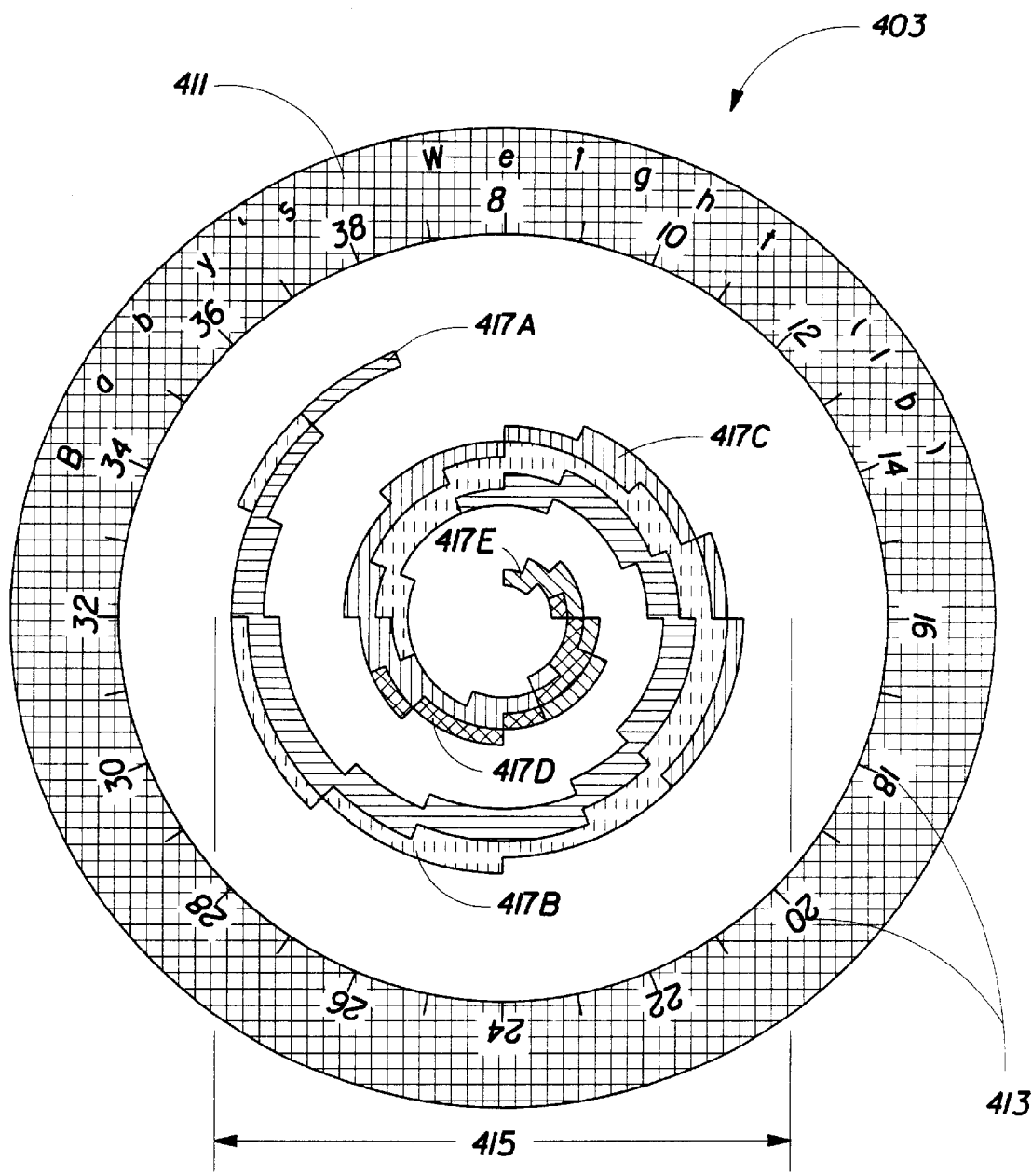
FIGS. 4B, 4C and 4D are plan views of respective components of a sizing guide wheel.
Figure 4C:
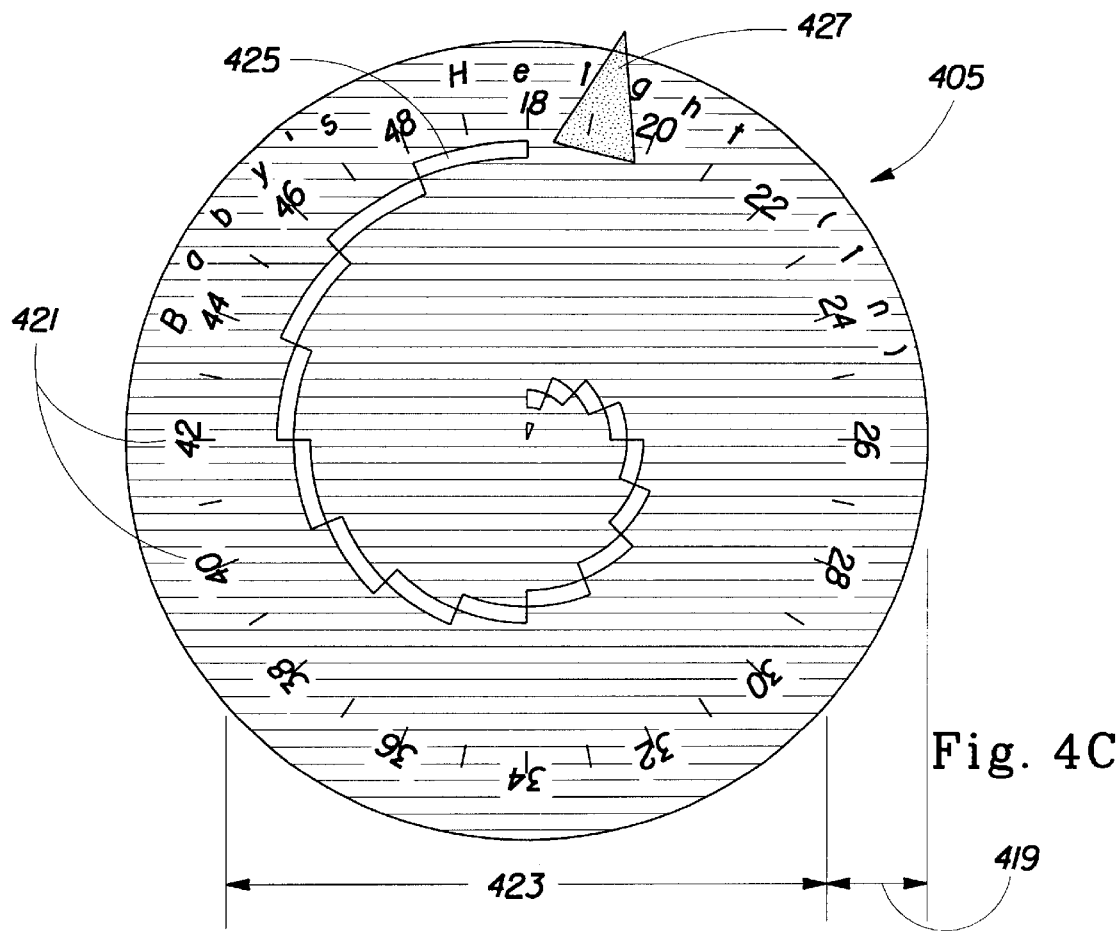
Figure 4D:
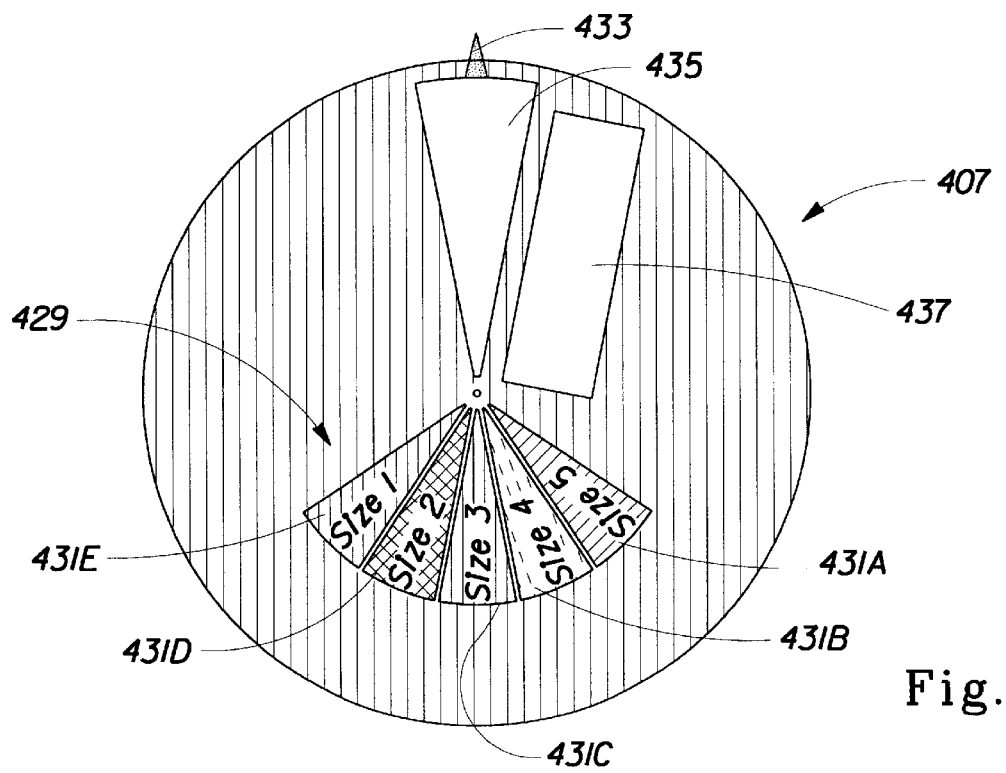

FIG. 4A illustrates an example of an interactive mechanical dial-type sizing wheel device for disposable infant diapers which embodies the present invention. Sizing wheel device 401 comprises a base wheel 403, a middle wheel 405, and a top wheel 407. The wheels are held together by an axle 409, the axle preferably having a broadened portion or cap at each end to keep the wheels from slipping off the axle. Both middle wheel 405 and top wheel 407 can be rotated around axle 409 relative to base wheel 403 and relative to each other. As shown in FIG. 4B, base wheel 403 has a radially outward portion 411 labeled with the indicia "Baby's Weight (Lb)" (wherein "Lb" means pounds) and with weight values 413 around the circumference of portion 411. As shown in FIG. 4B, base wheel 403 also has a radially inward portion 415 labeled with a spiral of a series of different-colored (or otherwise differentiated) segments 417a–417e, the different colors or other indicia for a series of segments corresponding to the different colors or other indicia in a diaper size key discussed hereinafter in connection with FIG. 4D. FIG. 4C shows middle wheel 405 having a radially outward portion 419 labeled with the indicia "Baby's Height (In)" (wherein "In" means inches) and with height values 421, and a radially inward portion 423 with a spiral of cutout segments or openings 425 designed to overly a portion of the different-colored segments on base wheel 403. Middle wheel 405 also has a pointer 427. As shown in FIG. 4D, top wheel 407 is labeled with a diaper size key 429 having five wedge-shaped segments 431a–431e. Each such wedge-shaped segment 431a–431e in diaper size key 429 has a different color, and each color corresponds to a respective color of different-colored segments 417a–417e on base wheel 403. Top wheel 407 also has a pointer 433, and a wedge-shaped cutout or opening 435 designed to overlie cutout segments or openings 425 in middle wheel 405. Other indicia 437, for example indicia of the brand or line of diapers to which sizing wheel 401 relates, can also be included on top wheel 407, or elsewhere on the sizing wheel 401. Further, the colors, sizes and shapes of any of the parts can be varied so long as the device works as intended.

Referring again to FIG. 4A, a user such as a consumer or other caregiver desiring diaper size guidance can "dial in" a value for a potential wearer's weight by rotating middle wheel 405 to move pointer 427 to point to the appropriate weight value 413 on base wheel 403. The user can also "dial in" a value for the potential wearer's height by rotating top wheel 407 to move pointer 433 to point to the appropriate height value 421 on middle wheel 405. Once the combination of a wearer height and a wearer weight value is dialed in, one of the segments 417a–417e from the base wheel 403 will be visible through the cut-out segments or openings 425 in middle wheel 405 as well as through the wedge-shaped cutout or opening 435 in top wheel 407 (in the example illustrated in FIG. 4A, the visible segment corresponds to a colored segment 417c). The user can then associate or match the color of the visible one of colored segments 417a–417e to one of the colors 431a–431e on diaper size key 429 which thereby identifies the size diaper predicted to be fit-appropriate for the wearer having the combined height and values dialed-in by the user (in the example illustrated in FIG. 4A, diaper Size 3). As will be apparent to a person skilled in the art from the disclosure of this embodiment of the invention, other mechanical devices such as a slide rule type device could be used in place of a sizing wheel to identify an appropriately sized garment, diaper or other absorbent article to a user of the device in a similar fashion.

The wearer characteristic information pertinent to providing the aforesaid size identification is preferably known to a person such as a typical consumer or other caregiver. There may be instances, however, where such information is not known by particular persons desiring such a size identification. In a further aspect of the invention, an apparatus may be provided which enable such persons to ascertain characteristic information which is not known and, in particular, may comprise apparatus for measuring or otherwise ascertaining the value of the pertinent characteristic for a particular wearer. Such apparatus may be associated with the articles as to which a size identification is to be provided, such as on or within the packaging for the articles, or may be associated with the charts, tables, lists or actively interactive devices which have been developed to provide such a size identification. By way of example, if a pertinent characteristic is wearer height, the device may be a height measurement scale on an in-store display next to which the intended wearer could stand or be held, and his or her height ascertained by the person. As another example, a measurement tape could be associated with or included within the packaging for the article. As a further example, a height measurement scale could be included on a changing pad upon which an infant is rested during diaper changes. If a pertinent characteristic is weight, a weight scale or other device for determining a potential wearer's weight could be associated with an in-store display. It will be apparent to those skilled in the art that other apparatus could be employed, depending on the wearer characteristic information to be determined and the context in which the apparatus is provided.

In developing the devices and methods of the present invention, it was found that at least an indirect yet reliable association can be developed between combined values of at least two selected wearer characteristics and the size or type of a given article which is best suited in terms of proper fit and/or functionality to a wearer who possesses particular values for such characteristics. In particular, it has been found that a reliable association can be developed based at least in part on a relationship between values of each of these characteristics and values of at least two other underlying wearer anthropometric attributes determined to be significant to fit. In regard to disposable diapers, a wearer's waist circumference, thigh circumference, and rise have been determined to be fit-significant. As used herein, "waist circumference" can be considered the circumference of the wearer's waist measured at the navel. "Thigh circumference" can be considered the circumference of a wearer's thigh measured as close to the crotch as possible while the wearer is standing (if the wearer cannot stand, then the measurement can be made while the wearer is lying down). "Rise" can be considered the distance from the wearer's navel to the lumbar curve of the back (the small of the back), measured through the crotch. It should be understood, however, that other dimensions and/or measurements from a wearer may provide fit-significant data that could be used in the device or method of the present invention.

It is apparent that although such wearer anthropometric attribute values may be significant to the fit of wearable articles, some or all of these attribute values, and their relationship to fit, are not typically known to a person such as a consumer who desires assistance in identifying a properly sized article for such wearers. As used herein, the term "consumer" refers to a person who purchases or otherwise selects such products for their own use or for use by other wearers, such as an infant. However it has further been found, in the course of developing the present invention, that it is possible to predict, with reasonable certainty, the values of at least two fit-significant anthropometric attributes from the values of at least two wearer characteristics which are typically known by or are at least readily ascertainable by persons such as consumers. For example, it has been found that relationships can be developed which can be used to predict a wearer's waist circumference, thigh circumference and rise from the values of a wearer's height and weight, or age and weight. Mathematical functions can be developed to represent these relationships, as described below. As is apparent, as used herein, a wearer "characteristic" may itself be an anthropometric characteristic, such as height, or some other characteristic, such as age.

One way that the above-described relationships can be determined is by first obtaining information regarding the characteristics and anthropometric attributes of potential wearers of the kinds of articles of interest, such as disposable diapers, and identifying those attributes which are significant to the fit of such articles on the wearers. Preferably, such information is obtained from a representative population of potential wearers. By "representative population", it is meant that the population encompasses wearers representing the range of values of anthropometric attributes and other characteristics that would be expected in the general population of potential wearers and which could be reasonably expected to have relevance to the fit of the pertinent article on such wearers. In determining such relationships in connection with disposable diapers, for example, a representative population ideally would include babies representing all age groups that would be expected to wear such diapers, and would further include babies within each age group representing the range of values of relevant anthropometric attributes and other characteristics (for example, waist circumference, thigh circumference, rise, height and weight) that could reasonably be expected of babies of that age. Further, a representative population would also ideally include babies of various ethnic backgrounds, or if potential wearers from a particular geographic region are of interest, babies of ethnic backgrounds relevant to that region. Alternatively, a subset of the above population could be used, such as babies representative of a particular age group or groups, along with other babies in other age groups sufficient to allow extrapolation from the representative age group(s) to such other age groups. If it is only desired to determine the aforesaid relationships and mathematical functions for a particular subset of the population, for example for babies that would be reasonably expected to wear only one or two diaper sizes, the population could also be limited accordingly. Of course, depending on the quality of results desired, a lesser or greater population of wearers could be employed. Values of relevant anthropometric attributes and information regarding other characteristics can often be obtained from the population of wearers employed by taking measurements of the individual wearers making up the population. If a value is not directly measurable, such as the individual's age, the values can be typically be obtained from the wearer or the wearer's caregiver.

Information regarding which anthropometric attributes are significant to the fit of articles on a wearer can be obtained, for example, by having the above-described population actually wear such articles and evaluating the fit relative to such attributes. The anthropometric attributes which are significant to fit can be identified through observation, measurement or by obtaining feedback from the wearer or the wearer's caregiver. Alternatively, as is known to those skilled in the art, historical data often exists which can be used to identify anthropometric attributes that are significant to fit. As previously described, in the case of disposable diapers it has been found that a wearer's waist circumference, thigh circumference, rise can be considered fit-significant anthropometric attributes regardless of the diaper design.

After fit-significant anthropometric attributes are identified, and the values of these attributes as well as the values of other wearer characteristics are obtained from a population of wearers, relationships between the values of such anthropometric attributes and such other characteristics can potentially be developed and defined mathematically. Before attempting to develop such relationships, it may be desirable to qualitatively assess the potential that particular wearer characteristics can be mathematically related in a meaningful fashion to certain fit-significant anthropometric attributes. Those characteristics which qualitatively appear to have such potential can then be selected to become the focus of the relationship determination, described below. At least two such wearer characteristics should be selected. Preferably, the selected characteristics will have "consumer-friendly" values, in other words, values which a typical consumer would likely know or could readily ascertain relative to a particular potential wearer. In the case of disposable diapers, such consumer-friendly characteristic values could include the wearer's age, height and/or weight.

Determining the relationships between the values of fit-significant anthropometric attributes and the values of two or more selected wearer characteristics may be accomplished by developing mathematical functions which mathematically represent the relationship between the values of each such anthropometric attribute and the values of the selected wearer characteristics. Using commercially available curve-fit and/or surface-fit computer software, and the values of a pertinent anthropometric attribute and selected characteristics obtained from the above-described wearer population, a mathematical function can be generated which may then be used for predicting the value of a fit-significant anthropometric attribute as a function of the values of selected wearer characteristics. The process can be repeated until such a mathematical function is produced for each fit-significant anthropometric attribute of interest. For example, a mathematical function may be generated that can be used to predict a wearer's waist circumference as a function of the wearer's height and weight values, and another mathematical function may be generated that can be used to predict a wearer's thigh circumference as a function of the values of the wearer's height and weight. As will be recognized by those skilled in the art, the functions can be tested, and predicted results compared to actual data to determine whether the reliability of the functions is acceptable. If the reliability is unacceptable, parameters of the curve-fit or surface-fit software may be adjusted to obtain functions which may provide more reliable predictions, or a different combination of fit-significant attributes and/or other wearer characteristics can be selected and used in an attempt to obtain a more reliable functions. Mathematical functions predictive of three anthropometric attributes (as a function of the values of the selected characteristics of height and weight, or age and weight) significant to the fit of disposable diapers are shown below in the EXAMPLES section. Other mathematical functions predictive of these anthropometric attributes in older children or adults, or functions predictive of other fit-significant anthropometric attributes as a function of the same or other selected wearer characteristics, may be ascertained in a similar fashion.

Once developed, the foregoing mathematical functions allow the values of underlying, fit-significant, wearer attributes to be determined from the values of at least two selected characteristics of potential wearers which are preferably known or readily ascertained by a person such as a consumer. In turn, this allows such attributes to be taken into account when developing an association between fit-appropriate size information and information regarding such other wearer characteristics. Because garments, disposable diapers and other absorbent articles are typically available in a variety of designs which may affect the fit of the article on a wearer, however, in addition to taking fit-significant wearer attributes into account it is also desirable to take the design of the particular article of interest into consideration when developing such an association. Disposable diapers, as one example, are presently available in various designs having different degrees of extensibility at the waist, legs and/or side panels, different fastening mechanisms, and so forth, which may affect fit.

The design of the article may be taken into consideration by wear testing various sizes of the article having the design of interest, preferably on an appropriate population of potential wearers, and developing a relationship between the values for the above-described fit-significant anthropometric attributes and a rating of how well an article of that design fits a wearer possessing particular values for such attributes. For example, a disposable diaper of a given design and size may be wear tested on a population of babies, the fit-significant anthropometric attribute values for each individual infant measured, and the fit of the diaper on the baby rated and related to the anthropometric attribute values. An appropriate population, in this instance, might include babies having a weight falling within the typical recommended weight range for the size diaper tested, as well as babies having weights falling near but outside the range, and representing a wide range of values of fit-significant anthropometric attributes and other selected characteristics for babies of such weights. Other considerations regarding selection of an appropriate population were discussed earlier herein. Wear testing of other sizes of a disposable diapers of the pertinent design can be conducted in a similar fashion.

As described below, as an alternative to such wear testing, normalized fit-significant attribute information can be employed to take the design of the garment, disposable diaper or other absorbent article into consideration.

The aforementioned wear testing fit ratings can be determined through observation, measurement, or by obtaining feedback from the wearer or the wearer's caregiver. The rating can be based on the overall fit of the article having the design of interest, or can be broken down into ratings of fit in selected areas such in the waist, in the crotch, around the thighs, or in other areas depending on the nature of the article. A relationship can also be developed between these design-specific fit ratings and values of the anthropometric attributes earlier determined to be of significance to fit regardless of design. By way of example, overall fit ratings can be compared to the values of each fit-significant anthropometric attribute which lead to that rating, and a relationship developed between the attribute values and the overall fit ratings of the article of a particular design and size using a linear regression or other appropriate relationship analysis. As another example, the fit of the article in a particular area can be compared to the values of particular fit-significant anthropometric attributes, and a relationship developed between the particular attribute values and the fit of the article in that area. These relationships can then be employed to predict a fit rating based on the values of fit-significant anthropometric attributes.

An association between a combination of values of the selected wearer characteristics and the size of a given article which is fit-appropriate for a wearer who possesses particular values for such characteristics can be determined by employing the above-described mathematical functions, the above-described fit-rating relationships and, desirably, a combined overall fit rating formula as described below. In particular, a value for two or more selected wearer characteristic can be input to a respective mathematical function to determine a predicted value for a respective fit-significant anthropometric attribute. The predicted anthropometric attribute value can then be used as input to the fit-rating relationship related to that attribute predict a fit rating for the disposable diaper or other absorbent article having the size and design of interest based on the value of that individual attribute. Preferably, the process is repeated in order to determine a fit rating based on the value of at least one or more of the other fit-significant attributes.

After individual predicted fit ratings are determined based on the values for the respective fit-significant anthropometric attributes, these individual fit ratings may be input to a formula developed to predict an overall fit rating as a function of the individual attribute ratings combined. A combined overall fit rating formula that may be used for predicting overall fit of diapers as a function of the combined attribute ratings is described below in the EXAMPLES section. The example formula contains weighting factors which give more or less weight to the fit rating relating to a particular anthropometric attribute, and were based on judgment developed in the course of reviewing historical consumer data. Other weighting factors or factors applying a different or equal weighting to each of the individual attribute ratings, however, could also be used.

If the results from the combined overall fit rating formula are judged to represent "good fit", the diaper or other absorbent article having a size which relates to the rating may be considered appropriate in terms of fit for a wearer possessing values for the selected characteristics which were input to the mathematical functions as described above. The process of determining an overall fit rating can be repeated using fit-ratings relationships developed for other sizes of the pertinent diaper or other article. The size which produces the best combined overall fit rating according to the formula can be considered the size expected to be the most fit-appropriate for a wearer who possesses the aforesaid values for the selected wearer characteristics. An association can then be made between these values of the selected wearer characteristics and the identity of a size of a given article which is predicted to be fit-appropriate for a wearer who possesses such values for such characteristics.

The above-described process of employing the mathematical functions, fit-rating relationships and combined overall fit rating formula can be repeated using other values for such wearer characteristics until an association between multiple values of such characteristics, or ranges of values, and the identity of a fit-appropriate size of the pertinent article is developed. As will be apparent to one skilled in the art, many of the foregoing steps can be automated such as through the use of a computer or computers to allow such steps to be completed in a relatively efficient fashion. Also, the process can be modified to include or emphasize certain factors which may be personally important to the consumer or caregiver, but less important to a population as a whole (i.e., the system can be customized by the user or consumer to help that person identify the proper article efficiently).

In a further aspect of the invention, normalized fit-significant attributes can be employed. A normalized fit-significant attribute takes into account both a fit-significant anthropometric attribute of a potential wearer and a related design attribute or attributes of a disposable diaper or other absorbent article. Once such normalized fit-significant attributes are developed, a prediction of how well a diaper or other absorbent article of a given size and having particular design attribute values will fit wearers possessing particular anthropometric attribute values can be made without wear testing an article of that size and design on potential wearers. Employing normalized fit-significant attributes also has the advantage of allowing design attribute and/or wearer anthropometric attribute values to varied, and the effect on fit of such variations to be predicted and evaluated, without such wear testing.

Normalized fit-significant attributes can be developed by initially identifying fit-significant anthropometric attributes of potential wearers relative to the kinds of articles of interest (such as disposable diapers) as described above, and then considering related article design attributes. For example, if waist circumference is identified as a fit-significant wearer anthropometric attribute for certain kinds of absorbent articles, then related design attributes of the article may include the circumference of the article's waist opening, the tension (if any) which is present at the waist opening at a particular circumference, the width of the front or back of the article near the waist, and so forth. After identifying relationships between particular fit-significant wearer anthropometric attributes and particular article design attributes, the relationships which are significant to fit can then be defined. The aforesaid normalized fit-significant attributes can then incorporate these defined relationships. In the case of disposable diapers, normalized fit-significant attributes which have been developed include a unitless ratio of the stretched width of the back of the chassis of a diaper design of interest to a potential wearer's waist circumference, a unitless ratio of the diaper leg opening dimension to a potential wearer's thigh circumference value, and/or a unitless ratio of the effective pitch of the chassis of the diaper to a potential wearer's rise value. A more detailed discussion of these normalized fit-significant attributes appears below in the EXAMPLES section.

Once normalized fit-significant attributes are developed, a relationship between values for the normalized attributes and absorbent article fit ratings can be determined. Because normalized attribute values are dependent on values of wearer anthropometric attributes as well as values of related article design attributes, a range of normalized attribute values can be evaluated relative to fit by wear testing an article of a particular design on a population of wearers representing the expected range of potential wearer anthropometric values, or by wear testing a variety of article designs representing a range of design attribute values on a lesser population of wearers, or ideally by wear testing a variety of article designs on a population of wearers representing the expected range of potential anthropometric values. Considerations regarding selection of an appropriate population were discussed earlier herein. Fit ratings, which can be related to values of a particular normalized attribute, can be determined through observation, measurement, or by obtaining feedback from the wearer or the wearer's caregiver during such wear testing. The fit ratings can be based on the overall fit of the diaper or other article, or can be broken down into ratings of fit in selected areas. For example, overall fit ratings can be compared to the values of a particular normalized fit-significant attribute which lead to that rating, and a relationship developed between the normalized attribute values and the overall fit ratings. Alternatively, the fit of the article in a particular area can be compared to the values of a particular normalized attribute, and a relationship developed between the particular attribute values and the fit of the article in that area. These relationships can be defined mathematically, such as through curve-fitting the fit rating and normalized attribute value information, as would be understood by a person skilled in the art. The mathematically-defined relationships can then be employed to predict an article fit rating based on values of the pertinent normalized fit-significant attribute.

After the above fit rating relationships are defined, an association between values of two or more selected wearer characteristics and the size of disposable diaper or other absorbent article of having particular design attributes which is fit-appropriate for a wearer who possesses particular values for such characteristics can be determined in a manner similar to that described previously. In particular, a value for each of the two or more selected wearer characteristics can be input to a respective mathematical function, as earlier described, to determine a predicted value for a respective fit-significant wearer anthropometric attribute. This predicted wearer anthropometric attribute value can then be employed in combination with pertinent design attribute values of the absorbent article having the size of interest to determine a value for the respective normalized fit-significant attribute. The normalized fit-significant attribute value can then be used as input to the pertinent fit-rating relationship to predict a fit rating for the absorbent article having such a size and design relative to a potential wearer who possesses such values for the two or more selected wearer characteristics. Preferably, the process is repeated in order to individually determine a fit rating based on the value of at least one or more other normalized fit-significant attributes.

Once predicted fit ratings are determined individually based on the values for the respective normalized fit-significant anthropometric attributes, these individual fit ratings may be input to a formula developed to predict an overall fit rating as a function of the individual normalized attribute fit ratings combined. A combined overall fit rating formula that may also be used for predicting overall fit of infant diapers as a function of the combined normalized attribute ratings appears below in the EXAMPLES section. As described earlier, the example formula contains weighting factors which give more or less weight to the fit rating relating to a particular normalized attribute. Other weighting factors or factors applying a different or equal weighting to each of the individual normalized attribute ratings, however, could also be used as desired.

If the results from the combined overall fit rating formula are within judged to represent "good fit", the article having a size and design which relates to the rating may be considered appropriate in terms of fit for a wearer possessing values for the selected characteristics which were input to the mathematical functions as described above. The process of determining individual and combined overall fit ratings can be repeated using design attribute values for other sizes of the article. The size which produces the best combined overall fit rating according to the formula can be considered the size expected to be the most fit-appropriate for a wearer who possesses the aforesaid values for the selected wearer characteristics. An association can then be made between these values of the selected wearer characteristics and the identity of a size of a given article which is predicted to be fit-appropriate for a wearer who possesses such values for such characteristics.

As previously described, and as will be appreciated by a person skilled in the art, many of the foregoing steps relating to a size assessment employing normalized fit-significant attributes can be automated such as through the use of a computer or computers to allow such steps to be completed in a relatively efficient fashion. Also, the process can be modified to include or emphasize certain factors which may be personally important to the caregiver, but less important to a population as a whole (i.e., the system can be customized by the user or consumer to help that person identify the proper article efficiently).

EXAMPLES

Method

The following is one example of a method which can be used to determine a reliable relationship or association between the values of at least two selected wearer characteristics and the size of a disposable diaper which is best suited in terms of fit for wearers who possess particular values for such characteristics, and which can be used to create a device of the invention. The method takes into account three underlying anthropometric attributes of potential wearers.

Disposable diapers of various sizes and designs were wear tested across a relatively large population of infants representative of those who are typically of diaper-wearing age. The tested population included babies possessing a wide range of anthropometric attribute values within each age group, such as various values of height, weight and other body-size attributes. Anthropometric attribute values were obtained by measuring each baby, the measurements typically including the baby's waist circumference (measured at the navel), thigh circumference (measured as near to the crotch as possible), and rise (the distance from the infant's navel to the lumbar curve or "small" of the back, measured through the crotch). Information regarding other characteristics, including the baby's age, height and weight, and the fit of the diaper on each baby, were also typically evaluated and recorded. Results of such testing were reviewed, and it was determined that the values of three baby anthropometric attributes were particularly important to disposable diaper fit regardless of the particular diaper design: the baby's waist circumference value, thigh circumference value, and rise value.

Because the values of a baby's waist circumference, thigh circumference, and rise are not typically known by a person such as a consumer who may desire size identification guidance in order to select a properly sized diaper for a baby, information regarding other infant characteristics was reviewed pursuant to developing a mathematical function that could be used to predict values for these three anthropometric attributes from values of other more readily known baby characteristics. Three mathematical functions were developed which reasonably predicted the value of a baby's waist circumference, thigh circumference, and rise from values of the baby's characteristics of height and weight. These mathematical functions were developed using TABLECURVE® 3D surface-fit software commercially available from SPSS, Inc. of Chicago, Ill.

In particular, baby waist circumference (in millimeters), height (in millimeters) and weight (in kilograms) values obtained from the aforementioned wearer testing was input to the surface-fit software and, using the software, the following mathematical function for predicting a baby's waist circumference value from values of the baby's height and weight was developed:

$$\text{Waist}=118.0067+(-0.00011684217 \times \text{Height}^2)+(127.41322 \times \text{Weight}^{0.5}).$$

Functions for predicting values of thigh circumference (in millimeters) and rise (in millimeters) were developed in a similar fashion, and are as follows:

$$\text{Thigh}=30.784119+(-0.017102501 \times \text{Height} \times \text{LnHeight})+ (102.85894 \times \text{Weight}^{0.5})$$ where LnHeight is the natural logarithm of the height; and $$\text{Rise}=26.656202+(31237.426/\text{Height})+(123.45999 \times \text{LnWeight})$$ where LnWeight is the natural logarithm of the weight.

It is noted that alternative mathematical functions could also be developed if desired to determine predictive relationships between other wearer attributes and characteristics. For example, during development of the present invention, the following mathematical functions were developed which reasonably predicted the values of a baby's waist circumference, thigh circumference, and rise from values of the baby's characteristics of age (in months) and weight:

$$\text{Waist}=98.643532+(-5.8876682 \times (\text{LnAge})^2)+(122.73184 \times \text{Weight}^{0.5})$$ where LnAge is the natural logarithm of the age;

$$\text{Thigh}=-10.988874+(-11.654004 \times \text{Age}^{0.5})+(101.49005 \times \text{Weight}^{0.5});$$

and $$\text{Rise}=81.440137+(-9.4998293 \times \text{LnAge})+(127.46251 \times \text{LnWeight})$$ where LnAge is the natural logarithm of the age and LnWeight is the natural logarithm of the Weight.

In developing the foregoing functions, the mathematically predicted results were compared to actual data, software parameters were adjusted, and the resulting functions again compared to actual data in an attempt to improve the reliability of the functions and resulting predictions. The mathematical functions identified above reflect this process, and are believed to provide reliable results. These functions are only examples, however, and it should be understood that other mathematical functions could be developed to provide reliable predictions of the values of fit-significant anthropometric attributes from values of other selected wearer characteristics.

After developing the above-described mathematical functions, disposable diapers having a design for which appropriate size identification information was desired were wear tested. The wear testing involved diapers of a particular size (e.g., Size 3) having the design of interest. These diapers were tested on babies possessing weight values representative of those who fell within the typical recommended weight range for diapers of the selected size and design, as well as babies whose weights fell outside but reasonably near the recommended range. The babies were also selected to represent a wide range of anthropometric attribute and other characteristic values, such as various values of height, weight and other body-size attributes. Anthropometric measurements were obtained from and values recorded for each infant, including the values for waist circumference, thigh circumference, and rise. Values for other selected characteristics, such as the baby's age, height and weight, also were recorded. The respective caregiver (typically a parent) for each infant was then requested to evaluate or "rate" the overall fit of the diaper (having the size and design worn) on the baby according to the following bilateral scale:

Overall Fit

+2 Much Too Large

+1 Somewhat Too Large

0 Just Right

−1 Somewhat Too Small

−2 Much Too Small

Figure 8:
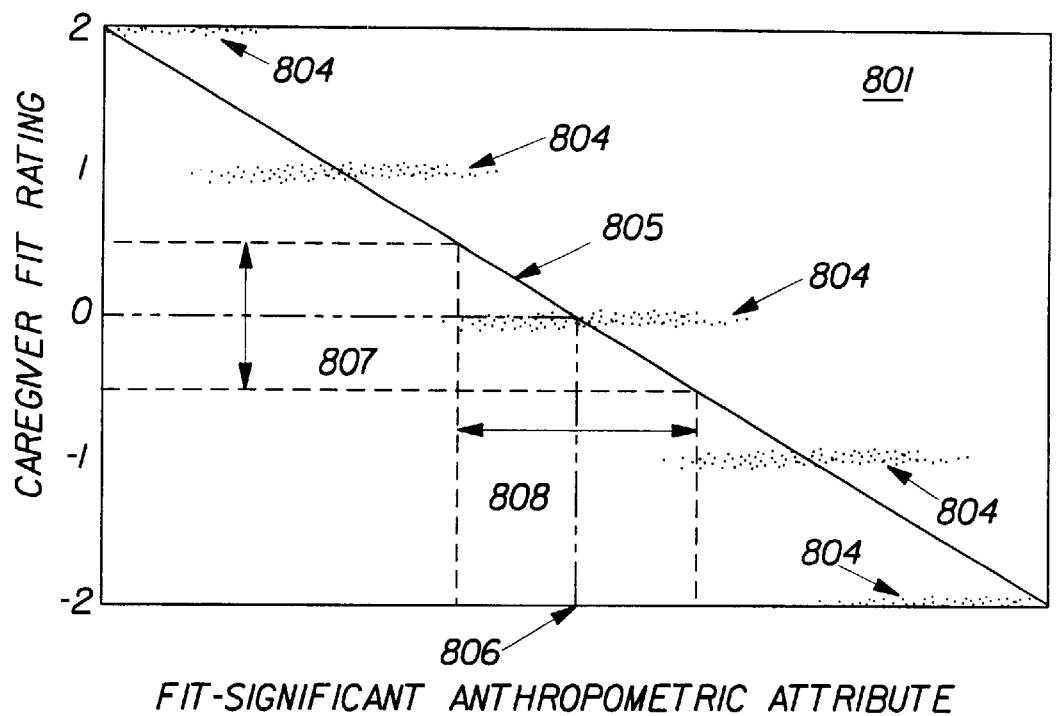
FIG. 8 is a simplified graphical view showing the relationship between certain fit ratings and wearer attributes.

Using a linear regression analysis, a linear relationship was developed between the results of the overall fit evaluations (hereinafter, "fit ratings"), for a diaper having the size and design tested, and values of baby waist circumference. The linear relationship allowed a fit rating to be predicted from a wearer waist circumference value. Other linear relationships were developed between the fit ratings and the values of baby thigh circumference, and between the fit ratings and the values of baby rise. The wear testing and overall fit evaluation process described above was repeated for other sizes of the diaper having the particular design of interest to obtain fit ratings for those sizes, and to develop related linear relationships between such fit ratings and values of baby waist circumference, thigh circumference, and rise. FIG. 8 illustrates an example of using the linear regression analysis to develop a relationship between fit ratings and the wearer's anthropometric measurements. Chart 801 plots the Caregiver Fit Rating (vertical axis) versus the Fit-significant Anthropometric Attribute (horizontal axis). Each individual point 804 on the chart represents a single caregivers fit rating based on the discrete −2 to +2 scale versus that baby's anthropometric attribute. (The points 804 were randomly adjusted by +/−0.125 in order to better view overlapping points, and more accurately visualize the actual distribution.) The relationship 805 is the linear fit through the points 804, and represents the "average" caregiver fit rating for a given anthropometric attribute. This relationship could have also been generated by breaking the anthropometric attribute axis into uniform brackets, calculating the average fit rating and distribution within that bracket and generating a continuous curve through those points. The target for the anthropometric attribute is that anthropometric attribute value 806 which will yield a zero for the fit rating in the relationship 805. The "just right" range 808 for the particular fit significant anthropometric attribute is that range 808 which yields a value on the Caregiver Fit Rating (vertical) axis in the range 807 of between −0.5 and +0.5. While linear relationships were developed and used in the present example, it should be understood that other appropriate relationships could also be developed and used, such as higher order polynomial relationships.

Figure 3:
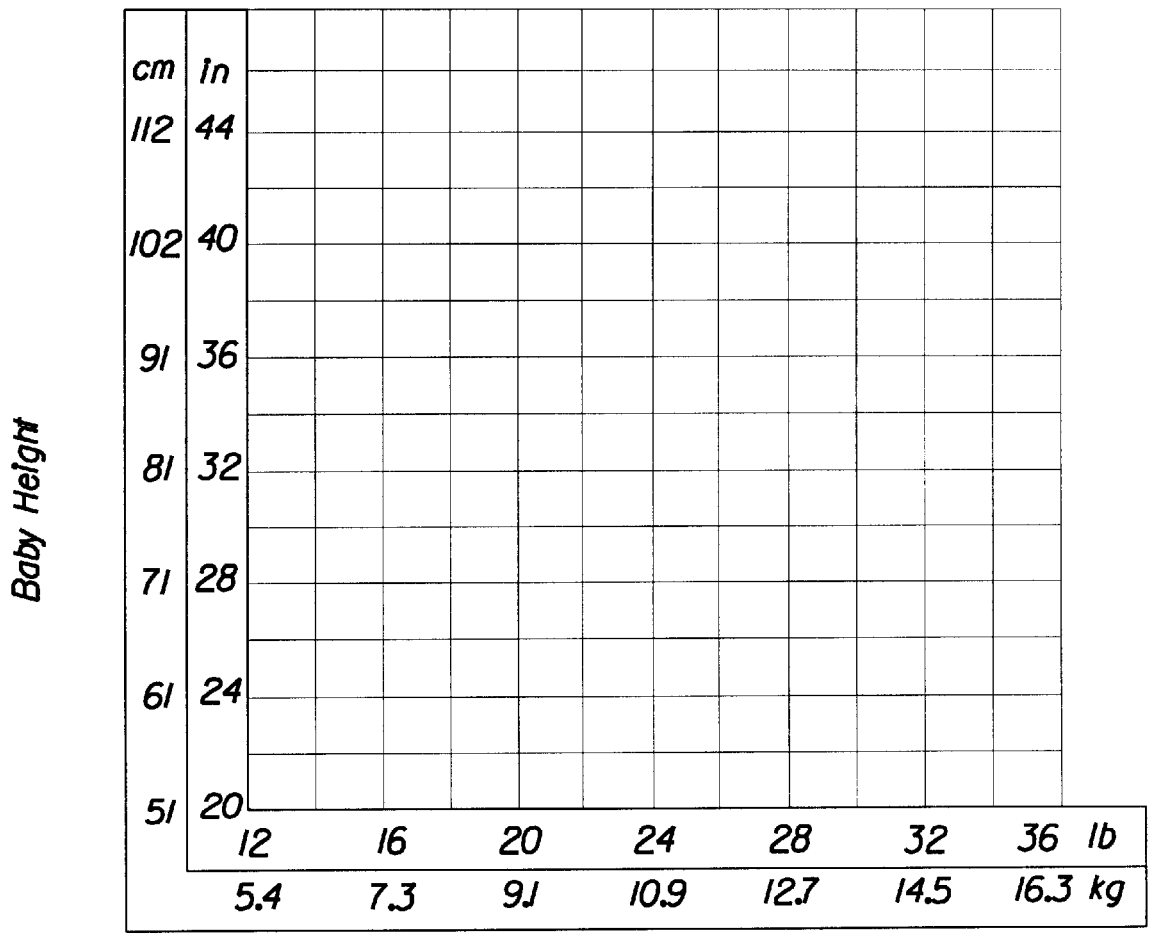
FIG. 3 is a plan view of a blank sizing guide.

A chart was then constructed having a vertical axis labeled or otherwise identified with the wearer characteristic "height", the vertical axis including height values expected for babies of diaper-wearing age, and a horizontal axis identified with the wearer characteristic "weight", the horizontal axis including weight values expected for babies of diaper-wearing age. The chart also included a grid forming a matrix of squares (as used herein, "squares" also contemplates rectangles) adjacent the axes. Such a chart, with the squares blank, is shown in FIG. 3. Height and weight values associated with each individual square in the matrix were then determined by locating the height value on the vertical axis and the weight value on the horizontal axis which corresponded with the respective squares's location in the matrix. The height and weight values associated with an individual square in the matrix were next input to the above-described mathematical functions to obtain corresponding function-predicted values for waist circumference, thigh circumference, and rise. The process was repeated until such function-predicted values for the three anthropometric attributes were obtained for each square. The dimensions of the square, shown here as 2 pounds on the horizontal edge by 2 inches on the vertical edge, are not limited to this, but could be any increment, larger or smaller, depending on the desired resolution of the chart.

After determining function-predicted values for waist circumference, thigh circumference, and rise for each square in the chart matrix, the above-described linear fit rating relationships developed relative to a diaper of a particular size (such as Size 3) being evaluated were used to predict three corresponding fit ratings for that size diaper in regard to a particular square. As described above, the closer the rating to zero, the better the predicted fit, with a rating in the range +0.5 to −0.5 corresponding to a prediction that the fit would be "just right". The three fit ratings for the particular square were then input to a formula developed to predict a combined overall fit rating as a weighted function of all three fit ratings combined. Although different formulas with different weightings could have been used, the formula used and found to work well for predicting combined overall fit was:

Combined Overall Fit=(0.342×(waist circumference fit rating))+ (0.279×(thigh circumference fit rating))+(0.379×(rise fit rating))

The foregoing weighting factors for the formula were determined using a least squares analysis of historical diaper wear test information. When the combined overall fit formula predicted a rating in the range +0.5 to −0.5 for the particular square relative to the size diaper being evaluated, it was judged that that sized diaper would fit appropriately on a potential wearer possessing values for the characteristics of height and weight associated with the particular square. However, in order to determine the size diaper predicted to most ideally fit such a potential wearer, the process of determining a combined overall fit rating relative to the particular square was repeated using the linear fit rating relationships developed for diapers of other sizes. The size which produced the best combined overall fit rating according to the formula (the rating closest to zero) was considered to be the size most appropriate for a baby possessing a combination of values for the characteristics of height and weight associated with the particular square, and the particular square was then identified with that size.

The foregoing process was repeated for each square in the matrix of the chart until each square was either identified with the most fit-appropriate diaper size or, in instances where the combined overall fit rating predicted that none of the diaper sizes considered would be fit-appropriate for a wearer having the characteristics associated with a particular square, or where no infants exist having the characteristics associated with a particular square, the particular square was not identified with any diaper size. Examples of completed charts are shown in FIGS. 1 and 2.

Normalized Fit-Significant Attributes

As described above, a normalized fit-significant attribute takes into account both a fit-significant anthropometric attribute of a potential wearer and a related design attribute or attributes of an article, and once developed can be used to predict how well an article of a given size and having particular design attribute values will fit wearers possessing particular anthropometric attribute values without wear testing an article of that size and design on potential wearers. Described below are three examples of normalized fit-significant attributes which have been developed for use relative to disposable diapers: a unitless ratio of the stretched width of the back of the chassis of the diaper design of interest to a potential wearer's waist circumference (hereinafter, "Percent Body Wrap"); a unitless ratio of the effective pitch of the chassis of the diaper to a potential wearer's rise value (hereinafter, "Navel to Back Ratio"); and, a unitless ratio of the diaper leg opening dimension to a potential wearer's thigh circumference value (hereinafter, "Percent Leg Stretch"). Functions are generated from consumer testing relating the normalized fit-significant attribute to the fit rating. These functions are valid for predicting the fit rating for any set of anthropometric attribute values, and for any size product whose fit range is to be determined. This is accomplished by calculating the normalized fit-significant attribute and inputting it into the function. The target value for each normalized fit-significant attribute is that value which yields a fit rating of zero in the function. This could be illustrated in a chart similar to that shown in FIG. 8, where the horizontal axis is a normalized fit significant attribute rather than the fit-significant anthropometric attribute shown in FIG. 8 and the function 805 is generated by relating the normalized fit-significant attribute to the consumers fit rating. The target value for this particular normalized fit-significant attribute is that value which yields a fit rating of zero in the function.

Percent Body Wrap

"Percent Body Wrap" is a unitless ratio of the width value of the back of a diaper chassis (including the extension or "stretch", if any, of the diaper side panels) relative to the waist circumference value of the potential wearer, and can be expressed by the following formula:

$$\text{Percent Body Wrap} = \frac{\text{Back Chassis Width} + (2 \times \text{Side Panel Extension})}{\text{Wearer Waist Circumference}}$$

Figure 5:
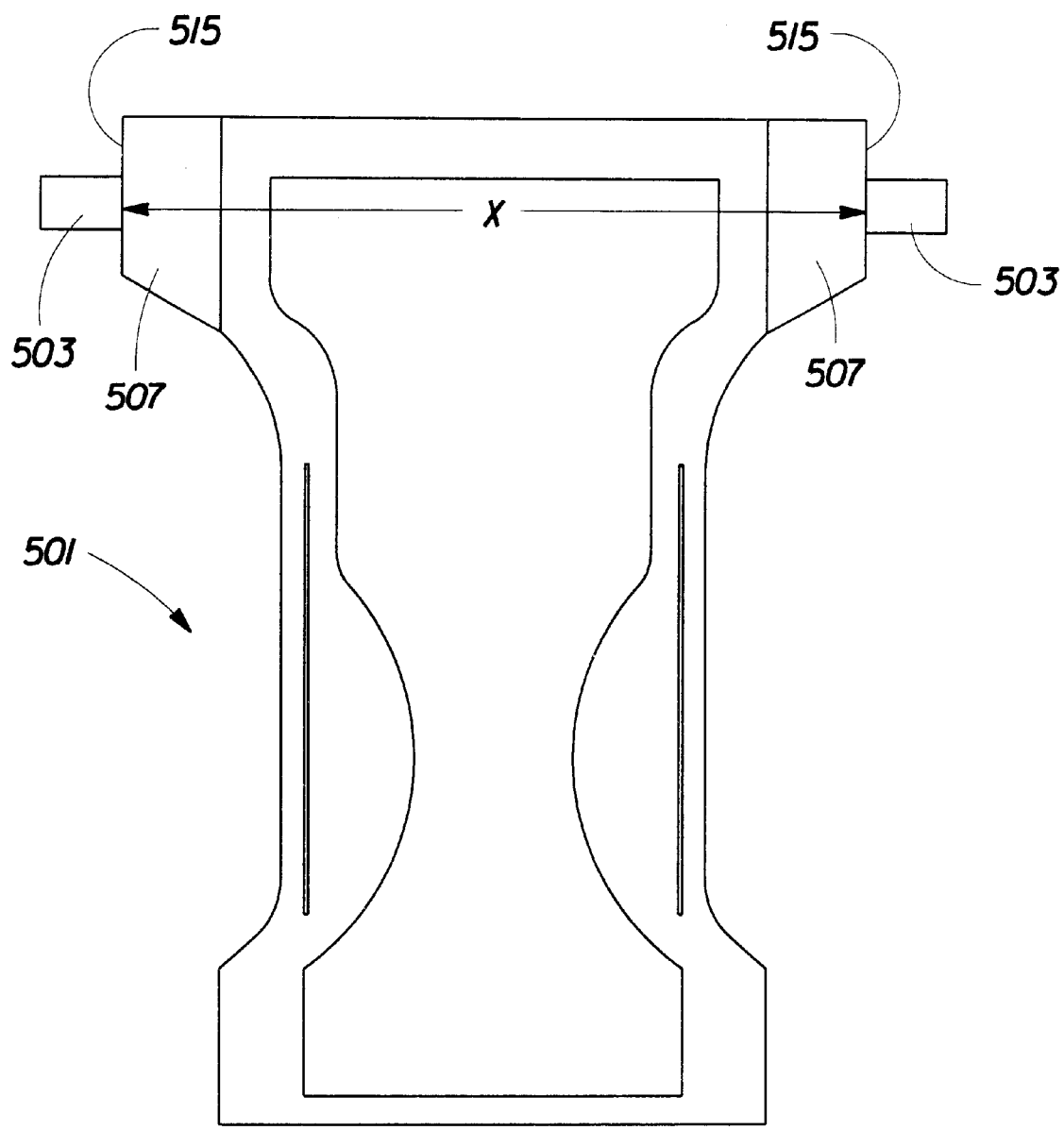
FIG. 5 is a simplified plan view of a diaper.

Referring to FIG. 5, "Back Chassis Width" is the value of the width of the back of a diaper chassis 501 of interest, and can be determined by measuring or calculating the distance "X" shown in FIG. 5 across the back of the chassis between respective locations where a diaper fastener 503 (such as a tape fastener) intersects the respective outer longitudinal edges 515 of diaper side panels 507 in the back of the chassis. The back of the diaper chassis between diaper side panels 507 is stretched when the measurement of the distance "X" is made; however, side panels 507, if extensible, are not extended as their extensibility (if any) is taken into account by the "Side Panel Extension" value. If the diaper has any contractive elastic features at the back waist region, such as a contracted waist stretch panel, then the distance "X" is measured while the contracted feature is fully stretched out to the original width of the back waist prior to the contraction. "Side Panel Extension" is the value of how much distance (if any) a respective side panel 507 of the diaper chassis 501 is extended under typical diaper application conditions, and can be determined by measuring the force versus extension properties of the side panel and the average force imparted to the side panel (such as by consumers or other caregivers) when the diaper is applied to a wearer. "Wearer Waist Circumference" is the value of the waist circumference of a potential wearer of interest, measured at the navel. All values are determined in consistent units, such as millimeters.

Navel to Back Ratio

"Navel to Back Ratio" (or "NTB Ratio") is a unitless ratio of the effective pitch (length) value of the diaper chassis relative to rise value of the potential wearer, and can be expressed by the following formula:

$$NTB\ Ratio = \frac{Effective\ Chassis\ Pitch}{Wearer\ Rise}$$

Figures 6A, 6B:
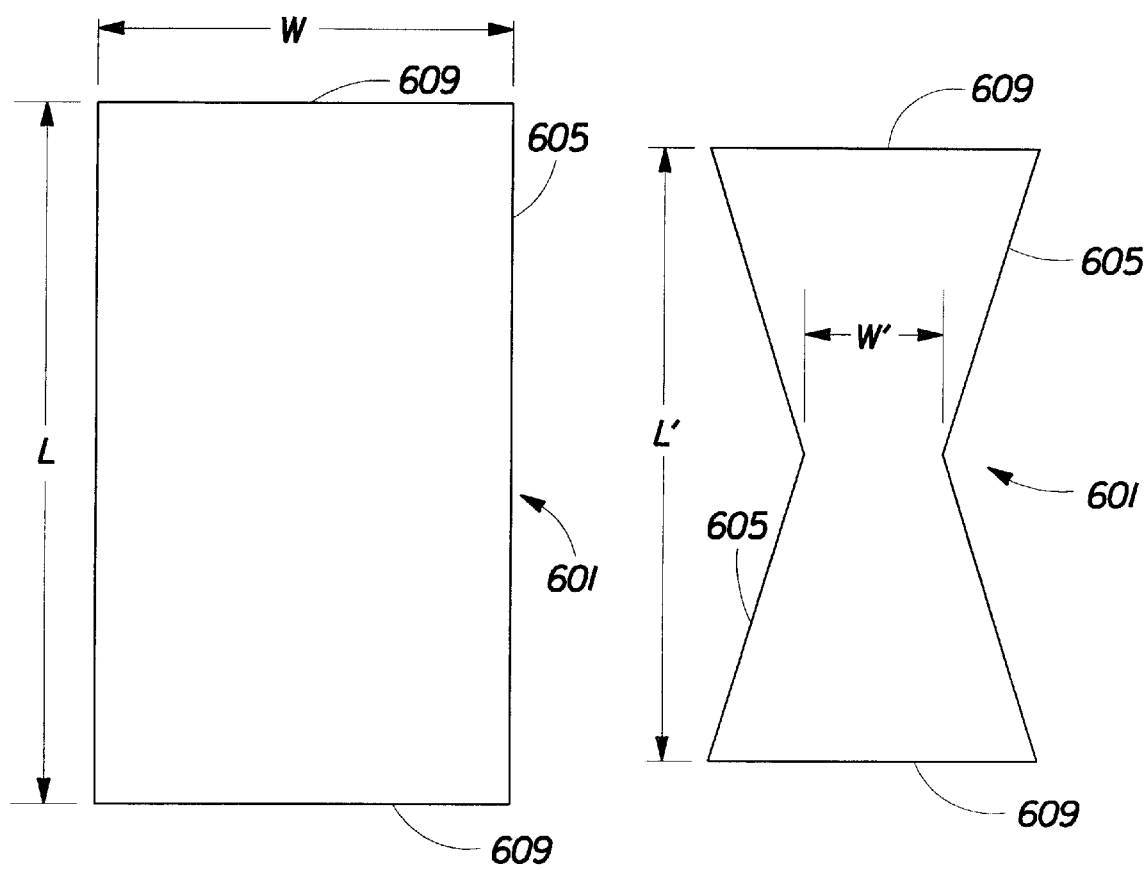
FIGS. 6A and 6B are, respectively, a simplified plan view of an unworn diaper chassis and a simplified plan view of a diaper chassis as worn.

"Effective Chassis Pitch" is the value of the average length between the lateral end edges of a diaper chassis of interest while the diaper is being worn. An average length value can be determined directly by measuring this length during wear testing of the diaper of interest on an appropriate population of wearers. Alternatively, with reference to FIGS. 6A and 6B, an average length value can be calculated. FIG. 6A shows, for purposes of illustration, an outline of a rectangularly-shaped diaper chassis 601 in plan view before the diaper is applied to a wearer. The diaper chassis in FIG. 6A has a length value of "L" between lateral end edges 609 and a crotch width of "W" between chassis longitudinal edges 605 at the crotch before being worn. FIG. 6B shows, for purposes of illustration, an outline of diaper chassis 601 in plan view after the diaper is applied on a wearer, having an "as worn" or narrowed crotch width of "W'" corresponding to the width of the crotch of an average wearer into which the crotch of chassis 601 is fitted (a reasonable estimate of an average infant crotch width is believed to be about 38 mm). As further shown is FIG. 6B, because the diaper chassis becomes narrowed as it is fitted into a wearer's crotch when worn, the length between the lateral end edges contracts and is effectively reduced to an "as worn" length "L'". The "Effective Diaper Length", "L'", can be calculated according to the following formula: Effective Diaper Length=$(L^2 - (W-W')^2)^{0.5}$. As would be apparent to a person skilled in the art, where the diaper chassis of interest contains notches for the crotch in the longitudinal edges, the deeper the notch the closer the effective diaper length "L'" will be to the unworn length "L" of the diaper. "Wearer Rise" is the distance from the navel to the lumbar curve of the back (the small of the back) of a potential wearer of interest, measured through the crotch. All values are determined in consistent units, such as millimeters.

In the case where the absorbent core parameters of a product whose fit rating is to be determined via this normalized attribute are different than the core parameters of the product used to generate the NTB Ratio versus fit rating function, the "NTB Ratio Target" and the NTB Ratio versus fit rating function should be adjusted to account for the different absorbent core parameters. This is important to consider because the absorbent core parameters can influence how the product fits through the crotch. The core parameters are the width of the absorbent core at the crotch of the infant, "CCW", and the thickness of the absorbent core at the crotch of the infant, "CCT" (shown in FIGS. 7–7A). (The core measurements should be taken from a product that has just been removed from a retail package and has not yet been worn or soiled) The NTB Ratio Target is the NTB Ratio value which yields a fit rating of zero in the function. The function should be adjusted such that the new NTB Ratio Target, "NTB Ratio Target$_{(new)}$", yields a fit rating of zero. The "NTB Ratio Target$_{(new)}$" can be calculated by first determining the Targeted Infant Rise for a given product size, "TIR$_{(size\ A)}$". The "NTB Ratio Target$_{(new)}$" should be calculated using two products of the same size, one product being the original product and the other being the product whose fit rating is being determined via the normalized attribute and which as different core parameters. The NTB Ratio Target is a unitless attribute with the same value for any product size.

$$TIR_{(size\ A)} = \frac{Effective\ Diaper\ Length_{(orig\ size\ A)}}{NTB\ Ratio\ Target_{(orig)}}$$

The core Adjusted Pitch, "CAP", for the two products is then determined. One product being the original product, "CAP$_{(ong\ size\ A)}$", which was used to generate the original NTB Ratio Target, "NTB Ratio Target$_{(orig)}$" and function. The other product being the one whose fit rating is being determined via this normalized attribute, and which has the different core parameters, "CAP$_{(new\ size\ A)}$".

$$CAP = ((TIR_{(size\ A)} + CCW + 2 \times CCT)^2 + (W-W')^2)^{0.5}$$

The variables CAP, CCW, CCT, & W are specific to each product. The variable TIR is specific to each product size.

$$NTB\ Ratio\ Target_{(new)} = NTB\ Ratio\ Target_{(orig)} \times \frac{CAP_{(new\ size\ A)}}{CAP_{(orig\ size\ A)}}$$

Figure 9:
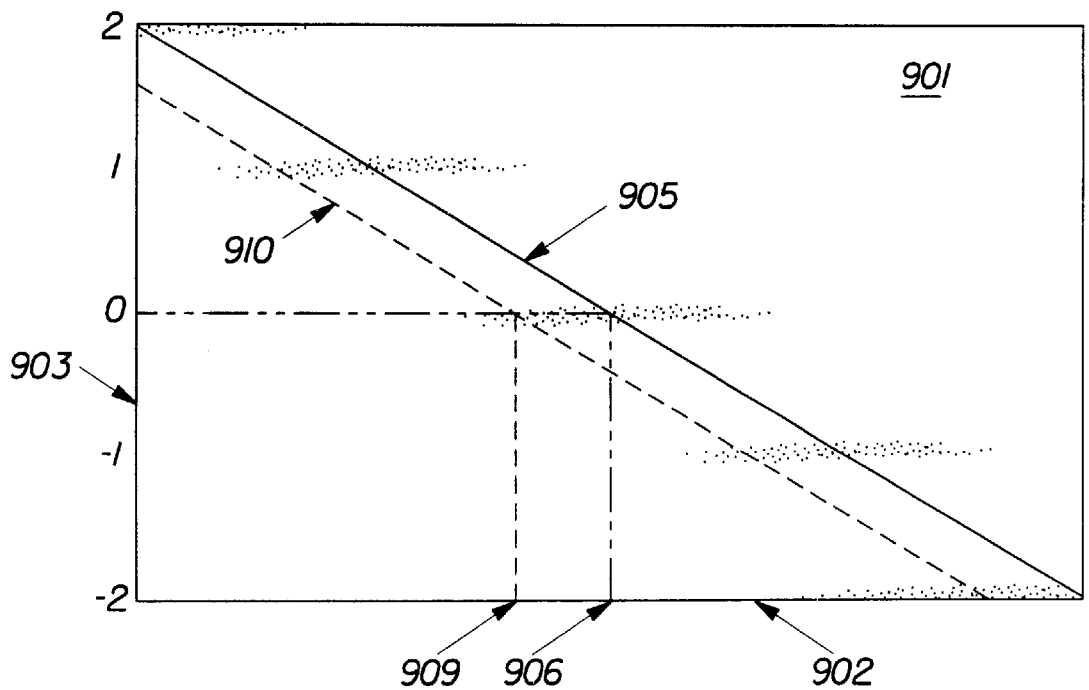
FIG. 9 is a simplified graphical view showing the relationship between certain fit ratings and wearer attributes.

The function is adjusted by shifting the curve parallel to the NTB Ratio axis such that the "NTB Ratio Target$_{(new)}$" yields a fit rating of zero. The "NTB Ratio Target$_{(new)}$" and the new function are valid for determining the fit rating for any size product whose core parameters are similar to the product used to calculate them. An example of such an adjustment is illustrated in chart 901 of FIG. 9, where the axis 902 is the NTB Ratio axis, point 906 represents the NTB Ratio Target $_{(orig)}$, and axis 903 is the fit rating axis. The function 905 is shifted parallel to the NTB Ratio axis 902, such that the NTB Ratio Target$_{(new)}$, 909 yields a fit rating of zero in the new function 910.

Percent Leg Stretch

"Percent Leg Stretch" is a unitless ratio of the value of the leg opening dimension of the diaper (including the extension or "stretch", if any, of the diaper leg cuff elastics and side panels) relative to the thigh circumference value of the potential wearer, and can be expressed by the following formula:

$$\text{Percent Leg Stretch} = \frac{\text{Diaper Leg Opening Dimension}}{\text{Wearer Leg Circumference}}$$

Figure 7:
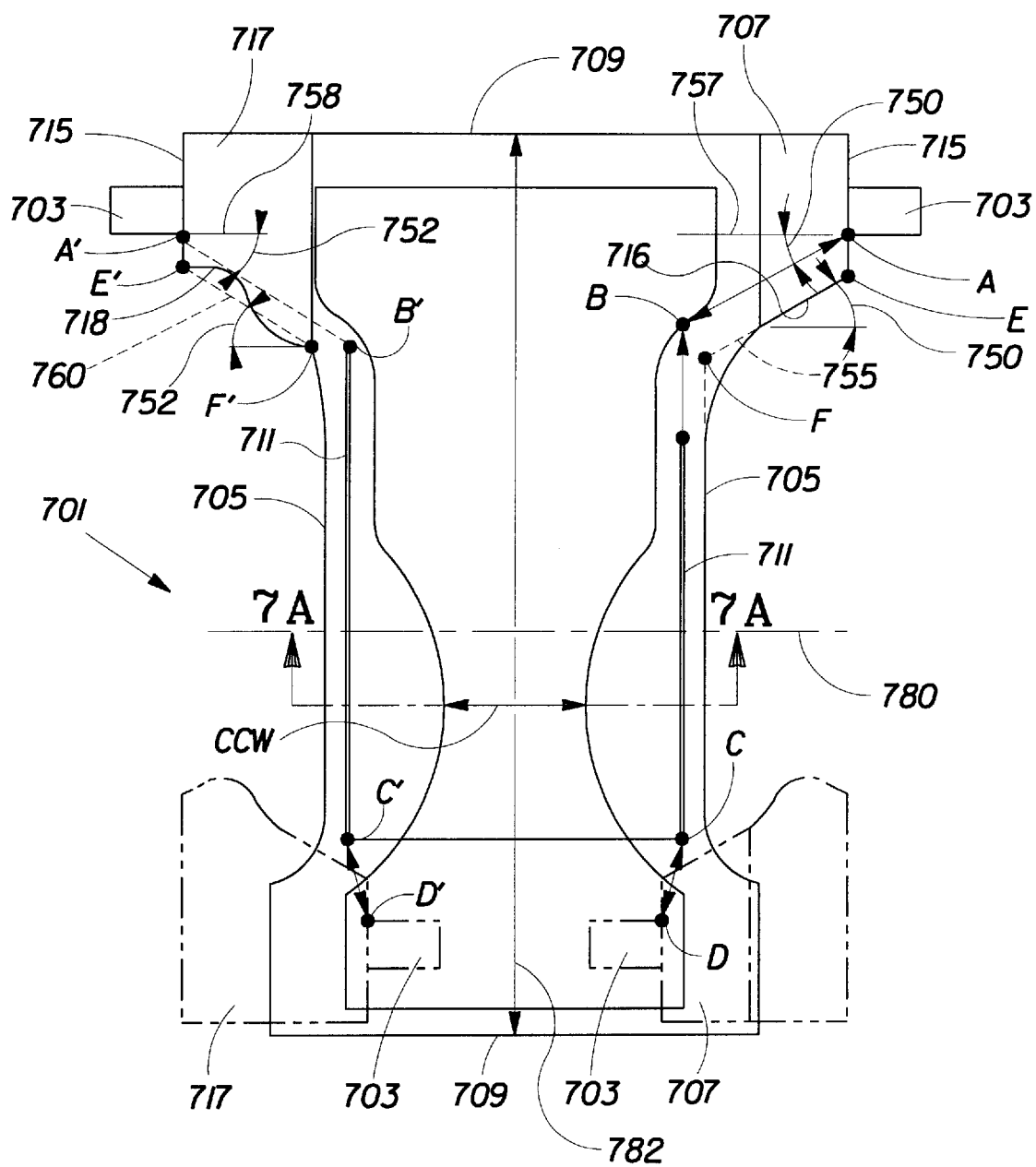
FIG. 7 is a simplified plan view of a diaper.
Figure 7A:
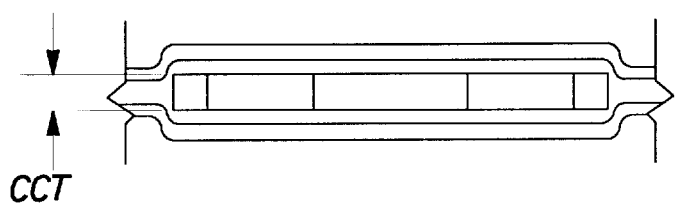
FIG. 7A is a cross-sectional view of the diaper of FIG. 7 taken through section line A—A.

Referring to FIG. 7, a "Diaper Leg Opening Dimension" value can be determined for the diaper of interest according to the following formula: Diaper Opening Dimension=AB+(Percent Cuff Contraction×BC)+CD. In FIG. 7, the diaper has a longitudinal centerline 782 and a lateral centerline 780. Also, in FIG. 7, there are two different exemplary side panels 707 and 717 joined to the chassis 701 in order to better illustrate how certain measurements are taken from different articles. The exact size and shape of the side panels 707 and 717 should not be construed as limiting in any way.

"AB" in the foregoing formula is the distance between point "A" and point "B" on diaper chassis 701 shown in FIG. 7, where point "A" is the point on the longitudinal edge 715 of diaper side panel 707 where the longitudinally inward edge of fastener 703 meets the side panel, and where point "B" is the point where a line drawn at an angle 750 from point "A" intersects a line extending from and in the same direction as diaper leg cuff elastic 711 (leg cuff elastic 711 is the outer leg cuff elastic if the diaper also has an inner barrier leg cuff). The angle 750 is the angle between the lateral centerline 780 (or a line 757 parallel to the longitudinal centerline 780) and a line 755 drawn between the two points E and F. Point E is the longitudinally inward corner of the side panel longitudinal edge 715. Point "F" is the intersection between the longitudinal edge 705 of the article and a straight line continued from longitudinally inward edge 716 of the side panel 707 when the bottom edge 716 of the side panel 707 is a straight line for at least half of the distance from side panel longitudinal edge 715 to the longitudinal edge 705 of the article, as shown in FIG. 7 (upper right corner). Thus, when measured, line AB should be parallel to line EF.

In embodiments wherein the longitudinally inward edge 718 of side panel 717 is not a straight line for at least half of the distance between side panel longitudinal edge 715 and longitudinal edge 705 of the article (as shown in the upper left corner of FIG. 7), point F' is the intersection of side panel 717 and the longitudinal edge 705 of the diaper chassis 701. In such cases, the angle 752 is the angle between the lateral centerline 780 (or a line 758 parallel to the longitudinal centerline 780) and a line 760 drawn between the two points E' and F', where point E' is the longitudinally inward corner of the side panel longitudinal edge 715. A'B' in the formula is the distance between point A' and point B' on diaper chassis 701, where point A' is the point on the longitudinal edge 715 of diaper side panel 717 where the longitudinally inward edge of fastener 703 meets the side panel 717, and where point B' is the point where a line drawn at an angle 752 from point A' intersects a line extending from and in the same direction as diaper leg cuff elastic 711. Thus, when measured, line A'B' should be parallel to line E'F'. (It should be clear to one of skill in the art that variables designated by letters including a single quotation mark or "prime" are intended to correspond to the letter designated variables not including the prime in the equations and disclosure herein, and that the variables including the prime mark are merely used to identify the values obtained from an alternative embodiment of the article being measured. Thus, for example, the "Diaper Leg Opening Dimension" value can be determined for an article of interest having a side panel structure according to the same formula as above with the primes of each of the variables substituted for the originally designated letter variables, i.e. the Diaper Opening Dimension=A'B'+(Percent Cuff Contraction ×B'C')+C'D'.)

If extensible, the extension of side panel 707 or side panel 717 should be taken into account when determining the distance between points "A" and "B" (in other words, the distance between points "A" and "B" should include the amount of any "in use" extension of side panel 707 or side panel 717). The "in use" extension of side panel 707 or side panel 717 can be calculated by determining the force versus extension properties of the side panel and the average force imparted to the side panel (such as by consumers or other caregivers) when the diaper is applied to a wearer. "BC" is the distance between point "B" described above and point "C" on diaper chassis 701, where point "C" is the end point of the diaper leg cuff elastic 711 in the front of the diaper. Because, as shown in FIG. 7, the diaper chassis is laid out flat when distance "BC" is determined, there will be some extension to leg cuff elastic 711. "CD" is the distance between point "C" described above and point "D" on the diaper chassis 701, where point "D" represents the location where point "A", described above, would be after fastener 703 is affixed to the front of the diaper during typical application to a wearer (the side panel and fastener location after such affixation are shown in phantom lines in FIG. 7, and are determined from information regarding the forces typically applied to the side panel upon application of the diaper to a wearer, and the force versus extension characteristics of the side panel).

"Percent Cuff Elastic Contraction" is the percentage of contraction of the leg cuff elastic 711 when it is released from the extended condition shown in FIG. 7 and allowed to contract the longitudinal edge 705 of the diaper chassis. One way that "Percent Cuff Elastic Contraction" for the diaper of interest can be determined by first cutting out a strip of chassis 701 near longitudinal edge 705, the strip including leg elastic 711 and the running the full length of the chassis. Each end of the chassis strip is then placed in a respective jaw on an Instron machine and the jaws are moved apart until the chassis strip is fully extended (the fully extended length of the strip should correspond to the length "L" of the chassis 701 when laid out flat as shown in FIG. 7). The jaws of the Instron machine are then caused to move towards on another, allowing the chassis strip to relax, until the Instron machine indicates that zero retraction force is being exerted on the jaws by the chassis strip. The percentage the chassis strip has retracted when the zero retraction force is reached is recorded as Percent Strip Retraction (it is believed that such a strip taken from infant diapers typically exhibit a percent retraction of between about 25–35 percent). "Percent Cuff Contraction" is calculated, using dimensions "BC" and "L" described above, according to the following formula: Percent Cuff Contraction=(BC−(Percent Strip Retraction/100×L))/BC.

In essence, the value determined for the Diaper Leg Opening Dimension as described above represents the size of the leg opening which would fit a wearer having an equal thigh circumference value without gapping and without extending the leg cuff elastic 711 beyond its contracted condition in the diaper. The "Wearer Thigh Circumference" value is the thigh circumference of a potential wearer of interest, measured as close to the crotch as possible. As will be recognized by one skilled in the art given the present disclosure, a "Percent Leg Stretch" value of greater than 100% (that is, when the "Diaper Leg Opening Dimension" value exceeds the "Wearer Thigh Circumference" value), may indicate potential gapping of the diaper at the leg opening (resulting in poor fit), and a "Percent Leg Stretch" value of significantly less than 100% (that is, when the "Wearer Thigh Circumference" value significantly exceeds the "Diaper Leg Opening Dimension" value) may indicate that the tension of the diaper around the leg will be excessive for such a wearer (also potentially resulting in poor fit). In this regard, a normalized attribute which utilizes information concerning the tension applied to the thigh by the diaper of interest could be employed as an alternative to percent leg stretch.

As described previously herein, a relationship between values for the foregoing normalized attributes and fit ratings can be determined, which can ultimately be used to predict the size of a diaper having the design attribute(s) of interest which is fit-appropriate for a wearer having particular anthropometric attribute values.

It should be understood that while particular embodiments and/or features of the invention of been described, it would be apparent to those skilled in the art (given the present description) that various other changes and modifications can be made without departing from the spirit and scope of the invention. Further, it should be apparent that all combinations of such embodiments and/or features are possible and can result in preferred executions of the invention. It is therefore intended to cover in the appended claims all such changes and modifications that are within the spirit and scope of the invention.

What is claimed is:

1. A device for identifying at least one size of an absorbent article which is appropriate for a potential wearer of the article, the device comprising:
    absorbent article size information;
    a first wearer characteristic including at least one wearer characteristic value;
    a second wearer characteristic including at least one second wearer characteristic value; and
    an association between the absorbent article size information and a combination of the first wearer characteristic and the second wearer characteristic wherein the association identifies an appropriate absorbent article size which is predicted to properly fit a wearer;
    wherein the absorbent article is a disposable diaper.

2. A device according to claim 1, wherein the appropriate absorbent article size covers a range of at least one of the first or second wearer characteristic values.

3. A device according to claim 1, wherein the device is selected from the group consisting of a chart, a graphic, a table, and a list.

4. A device according to claim 1, wherein at least a portion of the device is displayed on a medium selected from the group consisting of packaging materials, in-store display materials, advertising materials, and promotional materials.

5. A device according to claim 1, wherein at least a portion of the device is displayed on an electronic medium.

6. A device according to claim 1, wherein the device is displayed on a World Wide Web page.

7. A device according to claim 1, wherein the first wearer characteristic is height, and wherein the second wearer characteristic is weight.

8. A device according to claim 1, wherein the first wearer characteristic is age, and wherein the second wearer characteristic is weight.

9. A device according to claim 1, wherein the association is based at least in part on a relationship between the first wearer characteristic value and the second wearer characteristic value and at least one value for each of at least two different fit-significant anthropometric attributes of potential wearers of the absorbent article.

10. A device according to claim 9, wherein the at least two different fit-significant anthropometric attributes of potential wearers of the absorbent article include waist dimension and rise dimension.

11. A device according to claim 1, wherein the association is based at least in part on a relationship between the first wearer characteristic value and the second wearer characteristic value and at least one value for each of at least three different fit-significant anthropometric attributes of potential wearers of the absorbent article.

12. A device according to claim 11, wherein the at least three different fit-significant anthropometric attributes of potential wearers of the absorbent article include waist dimension, thigh dimension and rise dimension.

13. A device according to claim 1 wherein the association is based at least in part on a relationship between the first wearer characteristic value and the second wearer characteristic value and at least one value for each of at least two different normalized fit-significant attributes.

14. A device according to claim 13, wherein the at least two different normalized fit-significant attributes include Percent Body Wrap and NTB Ratio.

15. An interactive device for identifying at least one size of an absorbent article which is appropriate for a potential wearer of the article, the device comprising:
    absorbent article size information;
    a first wearer characteristic including at least one wearer characteristic value;
    a second wearer characteristic including at least one second wearer characteristic value; and
    an association between the size information and a combination of the first wearer characteristic and the second wearer characteristic;
    wherein the device allows a user of the device to input a value for at least one of the first wearer characteristic or the second wearer characteristic and which provides size information to the user which identifies an appropriate absorbent article size which is predicted to properly fit the wearer; and
    wherein the absorbent article is a disposable diaper.

16. An interactive device according to claim 15, wherein the device comprises at least one computer.

17. An interactive device according to claim 15, wherein the size information provided by the device is displayed on a medium selected from the group consisting of printed media and electronic media.

18. An interactive device according to claim 15, wherein the size information provided by the device is displayed on a World Wide Web page.

19. An interactive device according to claim 15, wherein the size information is provided in the form of sound.

20. An interactive device according to claim 15, wherein the device is a mechanical device.

21. An interactive device according to claim 15, wherein the first wearer characteristic is height, and wherein the second wearer characteristic is weight.

22. An interactive device according to claim 15, wherein the first wearer characteristic is age, and wherein the second wearer characteristic is weight.

23. An interactive device according to claim 15, wherein the association is based at least in part on a relationship between the first wearer characteristic value and the second wearer characteristic value and at least one value for each of at least two different fit-significant anthropometric attributes of potential wearers of the absorbent article.

24. An interactive device according to claim 23, wherein the at least two different fit-significant anthropometric attributes of potential wearers of the absorbent article include waist dimension and rise dimension.

25. An interactive device according to claim 15, wherein the association is based at least in part on a relationship between the first wearer characteristic value and the second wearer characteristic value and at least one value for each of at least three different fit-significant anthropometric attributes of potential wearers of the absorbent article.

26. An interactive device according to claim 25, wherein the at least three different fit-significant anthropometric attributes of potential wearers of the absorbent article include waist dimension, thigh dimension and rise dimension.

27. An interactive device according to claim 15 herein the association is based at least in part on a relationship between the first wearer characteristic value and the second wearer characteristic value and at least one value for each of at least two different normalized fit-significant attributes.

28. An interactive device according to claim 27, wherein the at least two different normalized fit-significant anthropometric attributes of potential wearers of the absorbent article include Percent Body Wrap and NTB Ratio.

29. An interactive device according to claim 15 wherein a user can input information which influences a weighting factor used to determine the association between the size information and a combination of the first wearer characteristic and the second wearer characteristic.

30. An interactive device according to claim 15 wherein a user can input information which influences an attribute target used to determine the association between the size information and a combination of the first wearer characteristic and the second wearer characteristic.

31. An interactive device according to claim 15 wherein the device also provides the user with a percentile rank of at least one of the wearer characteristic values.

32. A chart for identifying at least one size of an absorbent article which is appropriate for potential wearers of the article, the chart comprising:
   absorbent article size information;
   a first axis and a second axis, the first axis identifying a first wearer characteristic and the second axis identifying a second wearer characteristic; and
   an association between the absorbent article size information and a combination of the first wearer characteristic and the second wearer characteristic wherein the association identifies an appropriate absorbent article size which is predicted to properly fit a wearer;
   wherein the absorbent article is a disposable diaper.

33. A chart according to claim 32, wherein the first wearer characteristic is height, and wherein the second wearer characteristic is weight.

34. A chart according to claim 32, wherein the first wearer characteristic is age, and wherein the second wearer characteristic is weight.

35. A chart according to claim 32, wherein the association is based at least in part on a relationship between the first wearer characteristic value and the second wearer characteristic value and at least one value for each of at least two different fit-significant anthropometric attributes of potential wearers of the absorbent article.

36. A chart according to claim 35, wherein the at least two different fit-significant anthropometric attributes of potential wearers of the absorbent article include waist dimension and rise dimension.

37. A chart according to claim 32, wherein the association is based at least in part on a relationship between the first wearer characteristic value and the second wearer characteristic value and at least one value for each of at least three different fit-significant anthropometric attributes of potential wearers of the absorbent article.

38. A chart according to claim 37, wherein the at least three different fit-significant anthropometric attributes of potential wearers of the absorbent article include waist dimension, thigh dimension and rise dimension.

39. A chart according to claim 32 wherein the association is based at least in part on a relationship between the first wearer characteristic value and the second wearer characteristic value and at least one value for each of at least two different normalized fit-significant attributes.

40. A chart according to claim 39, wherein the at least two different normalized fit-significant anthropometric attributes of potential wearers of the absorbent article include Percent Body Wrap and NTB Ratio.

41. A method for identifying the size of an absorbent article that is predicted to be fit-appropriate for an intended wearer of the article, the method comprising the steps of:
   a. selecting a first wearer characteristic and a second wearer characteristic, each respective wearer characteristic having a range of values;
   b. developing an association between a combination of at least part of the range of values for the first wearer characteristic and at least part of the range of values for the second wearer characteristic and an absorbent article size which is predicted to be fit-appropriate for an intended wearer; and
   c. employing the association to provide information identifying the size of the absorbent article which is predicted to be fit-appropriate for the intended wearer;
   wherein the absorbent article is a disposable diaper.

42. A method according to claim 41 wherein the association of step (b) is developed from a second association between one or more fit ratings and a combination of at least part of the range of values for the first wearer characteristic and at least part of the range of values for the second wearer characteristic; and a third association between the one or more fit ratings and the absorbent article size which is predicted to be fit-appropriate for the intended wearer.

43. A method according to claim 42 wherein the second association is developed from a fourth association between one or more fit-significant anthropometric attributes and a combination of at least part of the range of values for the first wearer characteristic and at least part of the range of values for the second wearer characteristic; and a fifth association between the one or more fit-significant anthropometric attributes and one or more fit ratings.

44. A method according to claim 41, wherein the association is developed at least in part based on a relationship developed between at least one value for the first wearer characteristic and at least one value for the second wearer characteristic and at least one value for each of at least two different fit-significant anthropometric attributes of potential wearers of the absorbent article.

45. A method according to claim 44, wherein the at least two different fit-significant anthropometric attributes of potential wearers of the absorbent article include waist dimension and rise dimension.

46. A method according to claim 41, wherein said association is developed at least in part based on a relationship developed between at least one value for the first wearer characteristic and at least one value for the second wearer characteristic and at least one value for each of at least three different fit-significant anthropometric attributes of potential wearers of the absorbent article.

47. A method according to claim 46, wherein the at least three different fit-significant anthropometric attributes of potential wearers of the absorbent article include waist dimension, thigh dimension and rise dimension.

48. A method according to claim 41, wherein the association is developed at least in part based on a relationship developed between at least one value for the first wearer characteristic and at least one value for the second wearer characteristic and at least one value for each of at least two different normalized fit-significant attributes.

49. A method according to claim 48, wherein the at least two different normalized fit-significant anthropometric attributes of potential wearers of the absorbent article include Percent Body Wrap and NTB Ratio.

50. A method according to claim 41, wherein the information is provided visually or audibly.

51. A method according to claim 41 wherein the first wearer characteristic is height, and wherein the second wearer characteristic is weight.

52. A method according to claim 41, wherein the first wearer characteristic is age, and wherein the second wearer characteristic is weight.

53. A method according to claim 41, further comprising:
providing a measuring device for measuring at least one of the first or second wearer characteristic values possessed by the intended wearer.

54. A method according to claim 53, wherein the measuring device is capable of measuring the intended wearer's height.

55. A method according to claim 53, wherein the measuring device comprises a measuring tape.

56. A method according to claim 53, wherein the measuring device comprises a height scale on an in-store display.

57. A method according to claim 53, wherein the measuring device comprises a height scale on an infant diaper changing pad.

58. A device for identifying at least one size of an article which is appropriate for a potential wearer of the article, the device comprising:

article size information;

a first wearer characteristic including at least one wearer characteristic value;

a second wearer characteristic including at least one second wearer characteristic value; and an association between the article size information and a combination of the first wearer characteristic, the second wearer characteristic and at least one value of each of at least two different fit-significant anthropometric attributes of potential wearers of the article;

wherein the article is a diaper cover, underwear or swimwear.

59. A device according to claim 58 wherein the device allows a user of the device to input a value for at least one of the first wearer characteristic or the second wearer characteristic and which identifies an appropriate article size which is predicted to properly fit the wearer.

60. A device according to claim 58 wherein the device is a chart.

* * * * *